United States Patent
Lin et al.

(10) Patent No.: US 11,763,935 B2
(45) Date of Patent: Sep. 19, 2023

(54) CARE SYSTEM FOR PREDICTING BED EXIT AND PATIENT MANAGEMENT SYSTEM INCLUDING THE SAME

(71) Applicant: NATIONAL CHENG KUNG UNIVERSITY, Tainan (TW)

(72) Inventors: Chih-Lung Lin, Tainan (TW); Po-Ting Lee, Tainan (TW); Zong-Lin Yang, Tainan (TW)

(73) Assignee: NATIONAL CHENG KUNG UNIVERSITY, Tainan (TW)

(*) Notice: Subject to any disclaimer, the term of this patent is extended or adjusted under 35 U.S.C. 154(b) by 361 days.

(21) Appl. No.: 17/093,657

(22) Filed: Nov. 10, 2020

(65) Prior Publication Data
US 2021/0210198 A1     Jul. 8, 2021

Related U.S. Application Data

(60) Provisional application No. 62/961,656, filed on Jan. 15, 2020, provisional application No. 62/957,326, filed on Jan. 6, 2020.

(30) Foreign Application Priority Data

Jul. 17, 2020   (TW) .................... 109124306

(51) Int. Cl.
*G16H 40/20*     (2018.01)
*G16H 40/67*     (2018.01)
(Continued)

(52) U.S. Cl.
CPC ............ *G16H 40/20* (2018.01); *A61B 5/1115* (2013.01); *A61B 5/1116* (2013.01);
(Continued)

(58) Field of Classification Search
CPC ...... G16H 40/20; G16H 40/67; A61B 5/1115; A61B 5/1116; G08B 21/0461; G08B 21/0469; G08B 21/0476
(Continued)

(56) References Cited

U.S. PATENT DOCUMENTS

| | | | | |
|---|---|---|---|---|
| 7,378,975 | B1 * | 5/2008 | Smith | A61B 5/1126 340/666 |
| 2004/0178910 | A1 * | 9/2004 | Egger | G08B 21/22 340/556 |

(Continued)

FOREIGN PATENT DOCUMENTS

| | | |
|---|---|---|
| CN | 101833849 A | 9/2010 |
| CN | 107260427 A | 10/2017 |

(Continued)

OTHER PUBLICATIONS

Asbjørn, D et al., "Recognizing Bedside Events Using Thermal and Ultrasonic Readings," Sensors, Jun. 9, 2017, vol. 17, 19 pages.
(Continued)

*Primary Examiner* — Zhen Y Wu
(74) *Attorney, Agent, or Firm* — CKC & Partners Co., LLC

(57) ABSTRACT

A care system for predicting bed exit and suitable for a frame supporting a patient is provided. The care system includes a boundary-crossing detection system, a location sensing system, and a control circuit. The boundary-crossing detection system is coupled with the frame. The location sensing system is coupled with the frame, and is for obtaining relative position information between the patient and the frame. The control circuit is for data communicating with the boundary-crossing detection system and the location sensing system, and is for accessing care data defining multiple bed-exit behaviors. When one of following situations occurs, the control circuit transmits a warning signal:
(Continued)

(1) the control circuit determines that, according to the relative position information and the care data, a current behavior of the patient corresponds to one of the multiple bed-exit behaviors; and (2) the boundary-crossing detection system senses that an object is passing through.

17 Claims, 16 Drawing Sheets

(51) Int. Cl.
    *G08B 21/04*     (2006.01)
    *A61B 5/11*     (2006.01)

(52) U.S. Cl.
    CPC ..... *G08B 21/0461* (2013.01); *G08B 21/0469* (2013.01); *G08B 21/0476* (2013.01); *G16H 40/67* (2018.01)

(58) Field of Classification Search
    USPC ........................................................ 340/573.4
    See application file for complete search history.

(56) References Cited

U.S. PATENT DOCUMENTS

| | | | |
|---|---|---|---|
| 2006/0028350 A1* | 2/2006 | Bhai | A61B 5/1115 177/144 |
| 2006/0049936 A1* | 3/2006 | Collins, Jr. | G08B 21/028 340/539.11 |
| 2008/0272918 A1* | 11/2008 | Ingersoll | A61B 5/0002 600/595 |
| 2009/0278934 A1* | 11/2009 | Ecker | G06V 40/25 348/152 |
| 2011/0241886 A1* | 10/2011 | Receveur | A61B 5/1115 340/573.4 |
| 2012/0075464 A1* | 3/2012 | Derenne | A61B 5/0036 600/595 |
| 2013/0009778 A1* | 1/2013 | Bautovich | G07C 3/00 340/573.4 |
| 2013/0076517 A1* | 3/2013 | Penninger | A61H 3/00 5/81.1 R |
| 2014/0035749 A1* | 2/2014 | Reed, Jr. | A61B 5/1115 29/825 |
| 2014/0092247 A1* | 4/2014 | Clark | H04N 7/181 348/143 |
| 2014/0266733 A1* | 9/2014 | Hayes | A61G 7/05 600/484 |
| 2014/0324451 A1* | 10/2014 | Pesot | A61B 5/7475 705/2 |
| 2014/0343889 A1* | 11/2014 | Ben Shalom | A61B 5/1115 600/595 |
| 2015/0109442 A1* | 4/2015 | Derenne | H04N 7/185 348/143 |
| 2015/0261917 A1* | 9/2015 | Smith | G06F 21/6263 705/3 |
| 2015/0281659 A1* | 10/2015 | Hood | H04N 7/188 348/143 |
| 2016/0307429 A1* | 10/2016 | Hood | G16H 40/63 |
| 2017/0046577 A1* | 2/2017 | Rocque | A61B 5/1115 |
| 2017/0055882 A1 | 3/2017 | Al-Ali et al. | |
| 2017/0172827 A1* | 6/2017 | Schaaf | A61B 5/6801 |
| 2017/0325683 A1* | 11/2017 | Larson | A61B 5/002 |
| 2018/0158192 A1* | 6/2018 | Rocque | H04N 23/80 |
| 2019/0012546 A1* | 1/2019 | Kirenko | G06T 7/248 |
| 2019/0192052 A1* | 6/2019 | Weffers-Albu | A61B 5/14542 |
| 2019/0320987 A1* | 10/2019 | Halperin | G16H 40/63 |
| 2019/0388762 A1* | 12/2019 | Carney | A63B 69/3682 |
| 2020/0060910 A1* | 2/2020 | Lightcap | A61G 7/0516 |
| 2020/0245901 A1* | 8/2020 | Kaplan | G08B 21/22 |
| 2020/0405192 A1* | 12/2020 | Bhai | A61B 5/747 |
| 2021/0210198 A1* | 7/2021 | Lin | G16H 40/67 |
| 2021/0251579 A1* | 8/2021 | Nahavandi | A61B 5/6892 |

FOREIGN PATENT DOCUMENTS

| | | |
|---|---|---|
| TW | I397029 B | 5/2013 |
| TW | M456794 U1 | 7/2013 |
| TW | I425431 B | 2/2014 |
| TW | 201504997 A | 2/2015 |
| TW | I484446 B | 5/2015 |
| TW | M502925 U | 6/2015 |
| TW | I500000 B | 9/2015 |
| TW | I528333 B | 4/2016 |
| TW | M579024 U | 6/2019 |
| TW | I668658 B | 8/2019 |

OTHER PUBLICATIONS

Aung Aung Phyo Wai et al.,"Sleeping Patterns Observation for Bedsores and Bed-side Falls Prevention," 31st Annual International Conference of the IEEE Engineering in Medicine and Biology Society, Sep. 2, 2009, pp. 5087-6090, Minneapolis, Minnesota.

Chokemongkol Nadee et al., "Ultrasonic array sensors for monitoring of human fall detection," 2015 12th International Conference on Electrical Engineering/Electronics, Computer, Telecommunications and Information Technology (ECTI-CON), Jun. 24, 2015.

Carla Taramasco et al., "A Novel Monitoring System for Fall Detection in Older People," in IEEE Access, vol. 4, 12 pages, 2016.

Aki Härmä et al., "Bed exit prediction based on movement and posture data," IEEE-EMBS International Conference on Biomedical and Health Informatics (BHI), 2014, pp. 165-168.

Roberto L. Shinmoto Torres et al., "Sensor enabled wearable RFID technology for mitigating the risk of falls near beds," 2013 IEEE International Conference on RFID (RFID), 2013, pp. 191-198.

K.-H.Wolf et al., "Development and Pilot Study of a Bed-exit Alarm based on a Body-worn Accelerometer," Zeitschrift für Gerontologie und Geriatrie, Nov. 22, 2013, vol. 46, Issue 8, pp. 727-733.

Theresa Grant et al., "Measuring Sit-to-stand Timing Variability over Time using under Mattress Pressure Sensor Technology," IEEE International Symposium on Medical Measurements and Applications, Jun. 11, 2014.

Melanie Pouliot et al., "Differentiating Assisted and Unassisted Bed Exits using Ultrasonic Sensor," IEEE International Instrumentation and Measurement Technology Conference, May 13, 2012.

Heather Knight et al., "Chair Alarm for Patient Fall Prevention based on Gesture Recognition and Interactivity," 30th Annual International IEEE EMBS Conference, Aug. 20, 2008, pp. 3698-3701.

Marie Bruyneel et al., "Detection of Bed-exit Events Using a New Wireless Bed Monitoring Assistance," International Journal of Medical Informatics, Feb. 2011, vol. 80, No. 2, pp. 127-132.

Tian-Xiang Chen et al., "Bed-Exit Prediction based on Convolutional Neural Networks," IEEE International Conference an Applied System Innovation, May 13, 2017, pp. 188-191.

Brendan Chwyl et al., "DeepPredict: A Deep Predictive Intelligence Platform for Patient Monitoring," International Conference of the IEEE Engineering in Medicine and Biology Society Annual Conference, Jul. 11, 2017, pp. 4309-4312.

Yun Li et al., "Detection of Patient's Bed Statuses in 3D Using A Microsoft Kinect," International Conference of the IEEE Engineering in Medicine and Biology Society Annual Conference, Aug. 26, 2014, pp. 5900-5903.

Paul Bauer et al., "Modeling Bed Exit Likelihood In A Camera-Based Automated Video Monitoring Application," IEEE International Conference on Electro Information Technology, May 14, 2017, pp. 56-61.

Sheng-Yang Chiu et al., "A Convolutional Neural Networks Approach with Infrared Array Sensor for Bed-Exit Detection," IEEE International Conference on System Science and Engineering, Jun. 28, 2018.

* cited by examiner

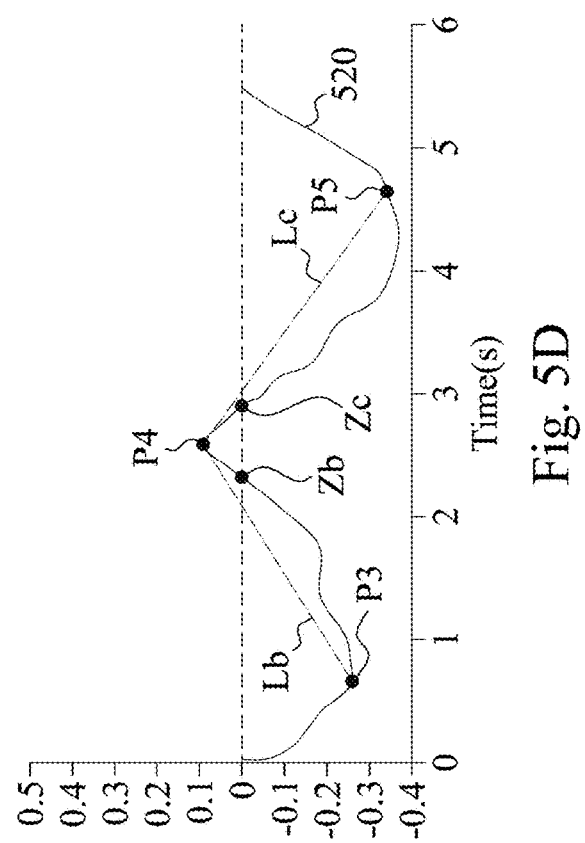
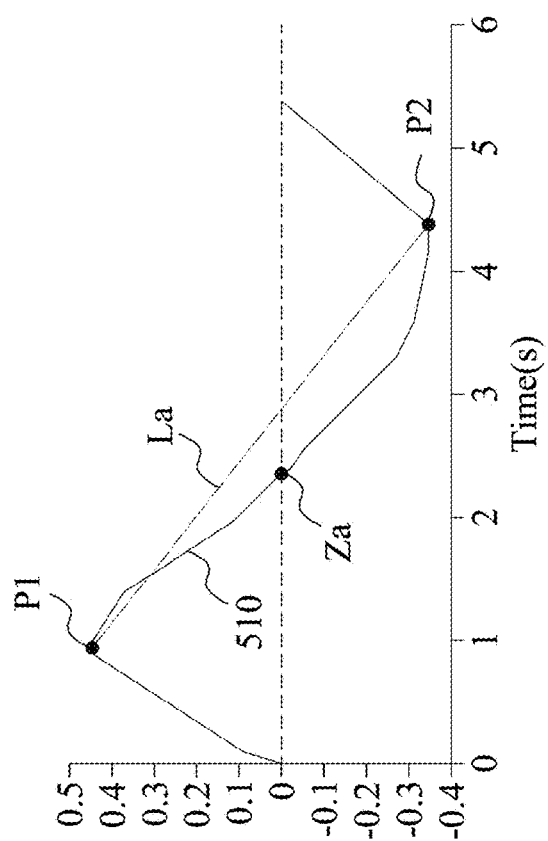
Fig. 5C
Fig. 5D

CARE SYSTEM FOR PREDICTING BED EXIT AND PATIENT MANAGEMENT SYSTEM INCLUDING THE SAME

RELATED APPLICATION

This application claims priority to Taiwan Application Number 109124306, filed Jul. 17, 2020, U.S. Provisional Application Ser. No. 62/957,326, filed Jan. 6, 2020, and U.S. Provisional Application Ser. No. 62/961,656, filed Jan. 15, 2020, all of which are herein incorporated by reference in their entireties.

BACKGROUND

Technical Field

The present disclosure generally relates to a care system and a patient management system. More particularly, the present disclosure relates to a care system and a patient management system for predicting bed exit.

Description of Related Art

As population ages, the demand for medical care for the elderly people has also increased. Most elderly people have osteoporosis, chronic diseases, etc., and thus they are often suffered from serious sequelae caused by falling down. In view of the fact that falls of the elderly people are usually caused by getting in and out of the bed by their own, the use of exit-bed alarm in medical institutions can reduce the occurrence of falls, so as to improve the safety of elderly hospitalization.

SUMMARY

The disclosure provides a care system configured to predict bed exit and suitable for a frame configured to support a patient. The care system includes at least one boundary-crossing detection system, a location sensing system, and a control circuit. The at least one boundary-crossing detection system is configured to be coupled with the frame. The location sensing system is configured to be coupled with the frame, and is configured to obtain relative position information between the patient and the frame. The control circuit is configured to data communicate with the at least one boundary-crossing detection system and the location sensing system, and is configured to access care data configured to define a plurality of bed-exit behaviors performed by the patient on the frame. When at least one of following situations occurs, the control circuit transmits a warning signal: (1) the control circuit determines that, according to the relative position information and the care data, a current behavior of the patient corresponds to one of the plurality of the plurality of bed-exit behaviors; and (2) the at least one boundary-crossing detection system senses that an object is passing through.

The disclosure provides a patient management system includes one or more care systems and a host device. Each care system is suitable for a frame configured to support a patient, and includes at least one boundary-crossing detection system, a location sensing system, and a control circuit. The at least one boundary-crossing detection system is configured to be coupled with the frame. The location sensing system is configured to be coupled with the frame, and is configured to obtain relative position information between the patient and the frame. The control circuit is configured to data communicate with the at least one boundary-crossing detection system and the location sensing system, and is configured to access care data configured to define a plurality of bed-exit behaviors performed by the patient on the frame. When at least one of following situations occurs, the control circuit transmits a warning signal: (1) the control circuit determines that, according to the relative position information and the care data, a current behavior of the patient corresponds to one of the plurality of bed-exit behaviors; (2) the at least one boundary-crossing detection system senses that an object is passing through. The host device is configured to data communicate with the control circuit to receive and display correspondingly the warning signal, and is configured to provide a host-terminal user interface. The host-terminal user interface includes one or more sensitivity adjustment images corresponding to the one or more care systems, respectively. Each sensitivity adjustment image is an user-interactive object. When the sensitivity adjustment image is moved from a first predetermined area to a second predetermined area, the control circuit of one of the one or more care systems corresponding to the sensitivity adjustment image changes the one of the plurality of bed-exit behaviors to other one of the plurality of bed-exit behaviors.

It is to be understood that both the foregoing general description and the following detailed description are by examples, and are intended to provide further explanation of the disclosure as claimed.

BRIEF DESCRIPTION OF THE DRAWINGS

FIG. 5C is for illustrating connecting lines formed by connecting coordinate points of the curve of FIG. 5A.

FIG. 5D is for illustrating connecting lines formed by connecting coordinate points of another curve.

DETAILED DESCRIPTION

Figure 1:
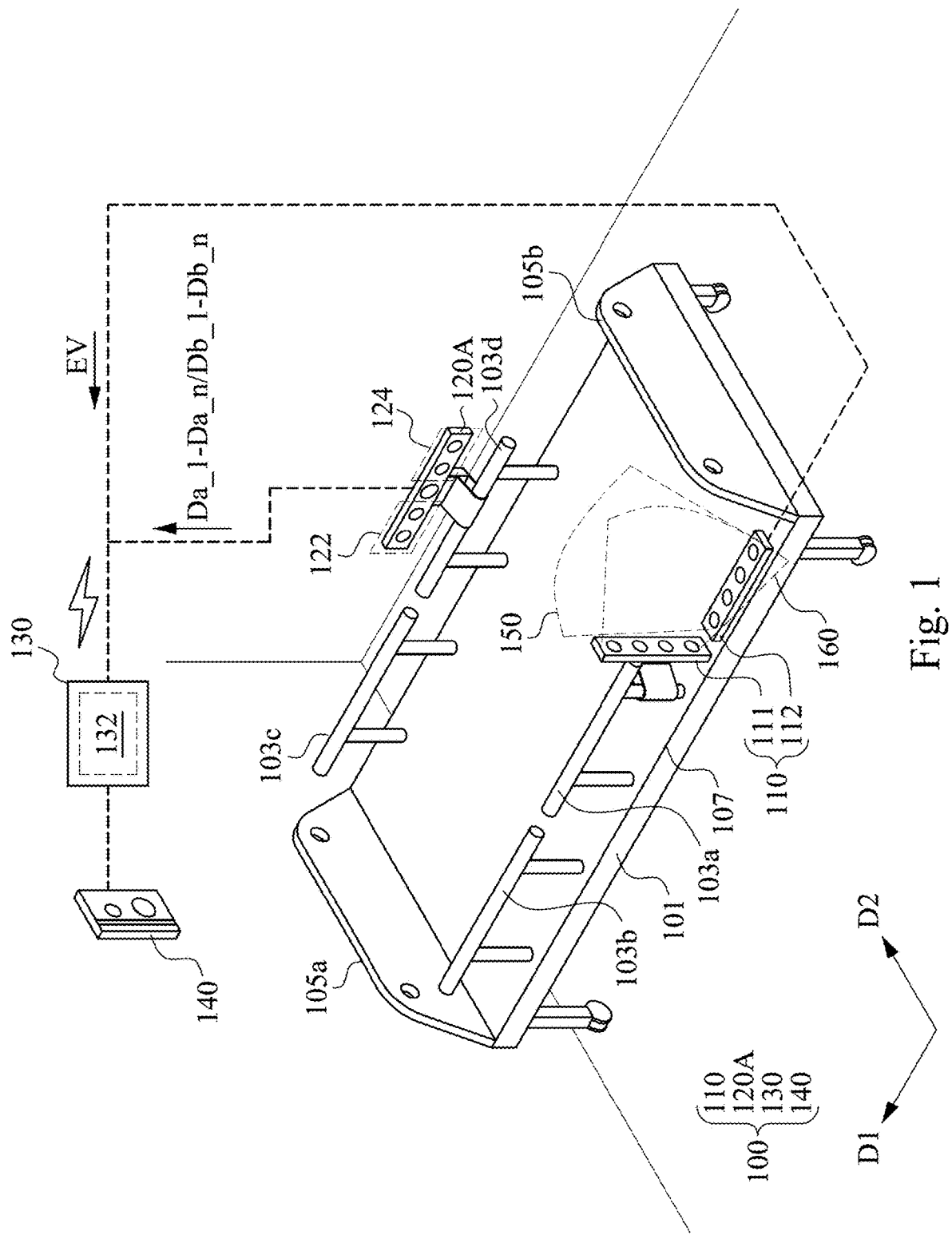
FIG. 1 is a schematic diagram of a care system according to one embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

FIG. 1 is a schematic diagram of a care system 100 according to one embodiment of the present disclosure. All components of the care system 100 may be disposed on a frame 101 configured to support a human body, or may be partially disposed on the frame 101 and partially disposed on a surrounding environment (e.g., a wall surface) of the frame 101. The frame 101 comprises multiple siderails 103a-103d can be raised up and lowered down, and comprises multiple plate components 105a-105b located at two ends of the frame 101, respectively. The siderails 103a-103d are disposed on multiple sides (e.g., a side 107) of the frame 101 in parallel with a first direction D1, and the plate components 105a-105b are disposed on multiple sides of the frame 101 in parallel with a second direction D2. In some embodiments, the frame 101 is a hospital bed for supporting a patient and a mattress. When the care system 100 detects a bed-exit behavior of the patient, the care system 100 can automatically inform healthcare workers to provide assistance to reduce fall injury events.

As shown in FIG. 1, the care system 100 comprises a boundary-crossing detection system 110, a location sensing system 120A, a control circuit 130, and an audio and video capturing device 140. The control circuit 130 is communicatively coupled with the boundary-crossing detection system 110, the location sensing system 120A, and the audio and video capturing device 140. The boundary-crossing detection system 110 is partially disposed at the siderail 103a, and partially disposed on an end, near the plate component 105b, of the side 107 coupled with the siderail 103a, so as to detect whether an object (e.g., body of the patient) passes through a space between the plate component 105b and the siderail 103a.

In this embodiment, the boundary-crossing detection system 110 comprises a first distance sensor 111 and a second distance sensor 112. The first distance sensor 111 is disposed at a side, near the plate component 105b, of the siderail 103a. The second distance sensor 112 is disposed on the side 107 and is between the siderail 103a and the plate component 105b. The first distance sensor 111 and the second distance sensor 112 have a first sensing area 150 and a second sensing area 160, respectively.

In some embodiments, when the siderail 103a is at an up position, the first sensing area 150 and the second sensing area 160 at least partially overlap with each other in space. When the object passes through the first sensing area 150 and/or the second sensing area 160, the boundary-crossing detection system 110 transmit an event notification EV to the control circuit 130. When the control circuit 130 receives the event notification EV, the control circuit 130 may transmits a warning signal through network by wire or wireless communication. For example, the control circuit 130 may transmit the warning signal to a host device 12, a cloud server 16, and a mobile device 18 of the healthcare worker in FIG. 10 which will be described later.

The aforesaid scenario that an object passing through may be that a portion of the object locating in the first sensing area 150 and/or the second sensing area 160 (e.g., the patient is sitting on the bedside), or may be that a portion of the object is moving in the first sensing area 150 and/or the second sensing area 160 (e.g., the patient is moving his/her arm or leg out of the bedside).

In some embodiments, the second distance sensor 112 may be disposed on an end, near the first distance sensor 111, of the plate component 105b. That is, the first distance sensor 111 and the second distance sensor 112 are disposed substantially in parallel and oppositely. In this situation, when the siderail 103a is at the up position, the first sensing area 150 and the second sensing area 160 also at least partially overlaps with each other.

In other embodiments, the care system 100 may comprise one or more boundary-crossing detection systems 110. Through a method similar to that described above, these boundary-crossing detection systems 110 can be disposed on the siderails 103a-103d; be disposed at multiple sides of the frame 101 in parallel with the first direction D1 and be arranged between the siderails 103a-103d and the plate components 105a-105b; or be disposed at the plate components 105a-105b. As a result, the care system 100 can detect bed-exit behaviors on multiple directions of the patient.

Figure 2:
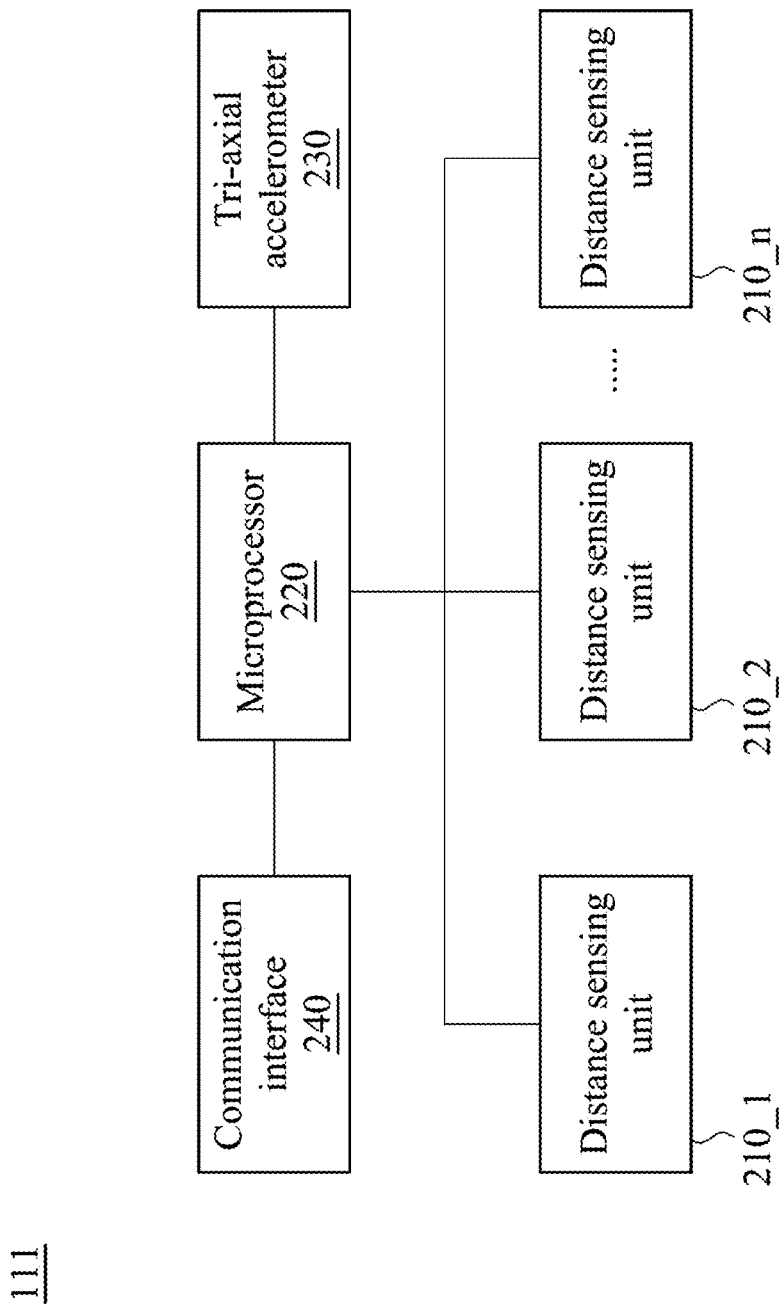
FIG. 2 is a simplified functional block diagram of the first distance sensor according to one embodiment of the present disclosure.

FIG. 2 is a simplified functional block diagram of the first distance sensor 111 according to one embodiment of the present disclosure. The first distance sensor 111 comprises multiple distance sensing units 210_1-210_n, a microprocessor 220, a tri-axial accelerometer 230, a communication interface 240, and a power module (not shown). The microprocessor 220 is coupled with each of the other functional blocks of FIG. 2, and the first distance sensor 111 is communicatively coupled with the control circuit 130 through the communication interface 240. In some embodiments, each of the distance sensing units 210_1-210_n comprises one or more infrared transceiver circuits so as to form the first sensing area 150 by multiple infrared light beams. The microprocessor 220 is configured to determine whether the object passes through the first sensing area 150 or not, and configured to transmit the event notification EV to the control circuit 130 through the communication interface 240. For the sake of brevity, other functional blocks of the first distance sensor 111 are not shown in FIG. 2.

The tri-axial accelerometer 230 is configured to transmit magnitude and/or a direction of an acceleration of the siderail 103a to the microprocessor 220 so that the microprocessor 220 can determine the placement position of the siderail 103a. When the microprocessor 220 determines that the siderail 103a has the acceleration substantially downward, the microprocessor 220 determines that the siderail 103a are switched from the up position to a down position. In this situation, the microprocessor 220 also transmits the event notification EV to the control circuit 130 through the communication interface 240.

The foregoing descriptions regarding the implementations, connections, operations, and related advantages of first distance sensor 111 are also applicable to the second distance sensor 112, that is, the second sensing area 160 are also formed by multiple infrared beams. For the sake of brevity, those descriptions will not be repeated here. In some embodiments, the tri-axial accelerometer 230 of the first distance sensor 111 and/or the second distance sensor 112 may be omitted.

Figure 3:
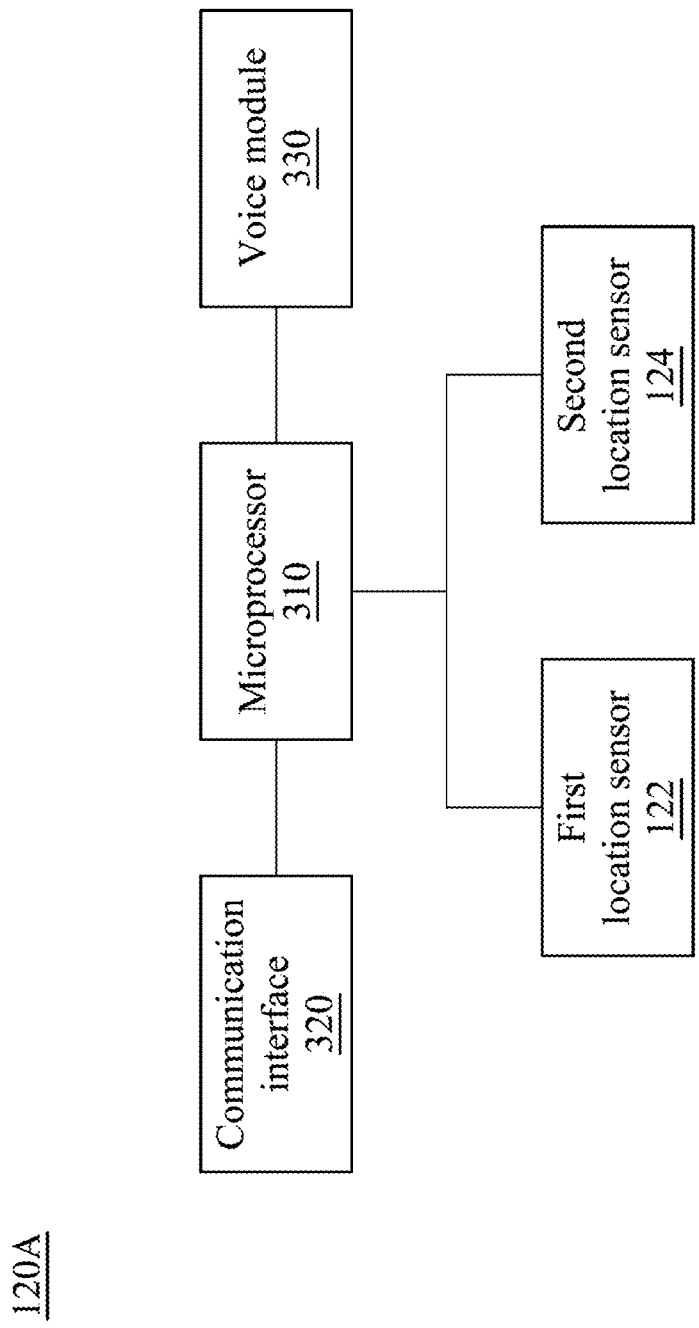
FIG. 3 is a simplified functional block diagram of a location sensing system according to one embodiment of the present disclosure.

Reference is made to FIG. 1 again. The location sensing system 120A is disposed at one of the siderails 103a-103d, and configured to obtain relative position information between the frame 101 and the patient on the frame 101, that is, to obtain information of the patient regarding body position or moving trend on the frame 101. Reference is made to FIG. 1 and FIG. 3, the location sensing system 120A comprises a first location sensor 122 and a second location sensor 124. A sensing direction of the first location sensor 122 is substantially aimed to the up-half portion of the frame 101 (e.g., the portion from a head of the bed to the middle of the bed). The first location sensor 122 is configured to sense for multiple times a position of a body portion of the patient which is in the up-half portion of the frame 101, so as to obtain multiple first distances Da_1-Da_n between the patient and the first location sensor 122. A sensing direction of the second location sensor 124 is substantially aimed to the bottom-half portion of the frame 101 (e.g., the portion from the middle of the bed to the end of the bed). The second location sensor 124 is configured to sense for multiple times a position of a body portion of the patient which is in the bottom-half portion of the frame 101, so as to obtain multiple second distances Db_1-Db_n between the patient and the second location sensor 124. Notably, the aforesaid relative position information comprises the first distances Da_1-Da_n and the second distances Db_1-Db_n.

In some embodiments, the first location sensor 122 and the second location sensor 124 have sensing areas that at least partially overlaps with each other. In practice, the first location sensor 122 and the second location sensor 124 each can be implemented by an ultrasonic distance measuring module.

As shown in FIG. 3, the location sensing system 120A further comprises a microprocessor 310, a communication interface 320, and a voice module 330. The microprocessor 310 is coupled with each of the other functional blocks in FIG. 3, and the location sensing system 120A is communicatively coupled with the control circuit 130 through the communication interface 320. The microprocessor 310 transmits, through the communication interface 320, the relative position information comprising the first distances Da_1-Da_n and the second distances Db_1-Db_n to the control circuit 130. The control circuit 130 calculates according to the relative position information and the care data 132 stored in advanced therein to determine whether a current behavior of the patient corresponds to one of multiple predetermined bed-exit behaviors. In some embodiments, the multiple predetermined bed-exit behaviors comprises lowering down the siderails 103a-103d, moving from the head of the bed (e.g., the plate component 105a) to the end of the bed (e.g., the plate component 105b), sitting on the bedside, and completely leaving the bed. The relative operation and determination process will be described in the following paragraphs. If the control circuit 130 determines that the patient is leaving the bed, the control circuit 130 can transmit the warning signal through network by wire or wireless communication. For instance, the control circuit 130 can transmit the warning signal to the host device 12, the cloud server 16, and the mobile device 18 of the healthcare worker in FIG. 10 to be described later.

In some embodiments, when the control circuit 130 transmits the warning signal, the control circuit 130 simultaneously instructs the voice module 330 of the location sensing system 120A to play a predetermined voice notification to prompt the patient to stop his/her bed-exit behavior. In this situation, the control circuit 130 may also enable the audio and video capturing device 140 to transmit real-time audio and video of the patient to, for example, the mobile device 18 of the later described FIG. 10. In other embodiments, the healthcare worker can conduct voice and/or video communication with the patient through the mobile device 18 and the audio and video capturing device 140 to discourage the patient from leaving bed.

Notably, the control circuit 130 of FIG. 1 may be implemented independently, or may be implemented within an outer case of the boundary-crossing detection system 110 or within an outer case of the location sensing system 120A. In some embodiments, the control circuit 130 can be integrated with the microprocessor 220 of FIG. 2 as a single chip, and thereby the communication interface 240 is configured to communicatively couple with the location sensing system 120A and the audio and video capturing device 140. In other embodiments, the control circuit 130 can be integrated with the microprocessor 310 of FIG. 3 as a single chip, and thereby the communication interface 320 is configured to communicatively couple with the boundary-crossing detection system 110 and the audio and video capturing device 140. That is, various implementations of the control circuit 130 are within the contemplated scope of the present disclosure from consideration of the teachings herein.

The communication interfaces of various embodiments of the present disclosure (e.g., the communication interfaces 240 and 320 of FIG. 2 and FIG. 3) may be implemented by hardware and/or software that comply with communication protocol of Bluetooth, Wi-Fi, ZigBee, cellular radio, or any other wireless communication technology, but this disclosure is not limited thereto. In some embodiments, the communication interfaces of the present disclosure may be communication interfaces using wire communication technology.

In addition, the control circuit 130 and the microprocessors (e.g., the microprocessor 220 and the microprocessor 310) of various embodiments of the present disclosure each can be implemented by single- or multi-chip general purpose processors, digital signal processors (DSPs), field programmable gate arrays (FPGAs), any other suitable programmable device, or the combination thereof.

The operations, performed by the control circuit 130 by using the first distances Da_1-Da_n and the second distances Db_1-Db_n, for determining whether the patient is performing a bed-exiting behavior will be described in reference with FIGS. 4A-4B and FIGS. 5A-5E in the following paragraphs.

Figure 4B:
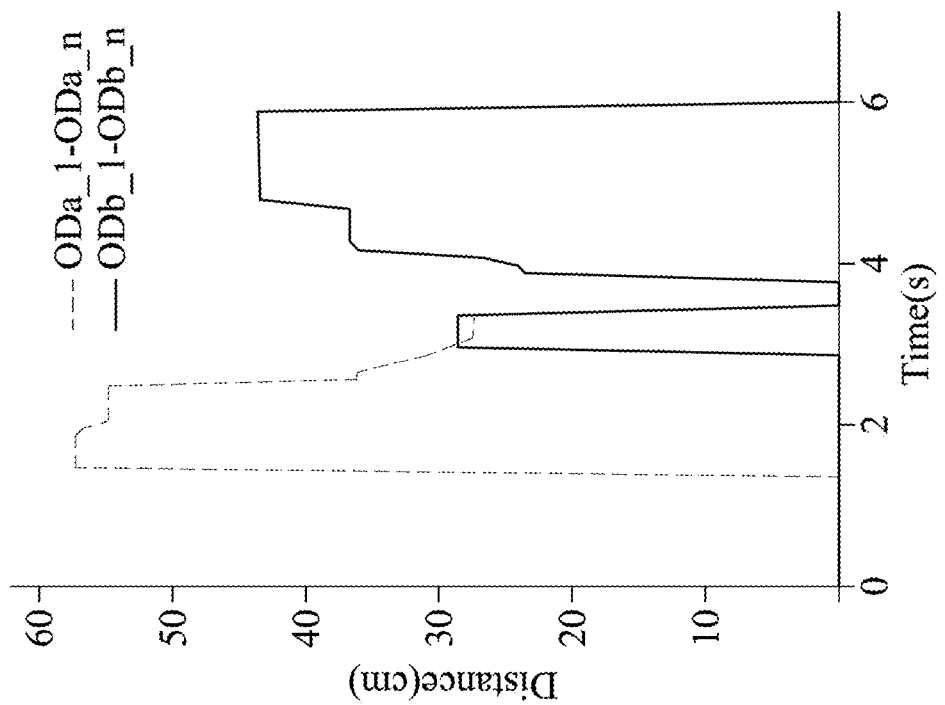
FIG. 4B shows an illustrative line chart depicted according to first optimized distances and second optimized distances.
Figure 4A:
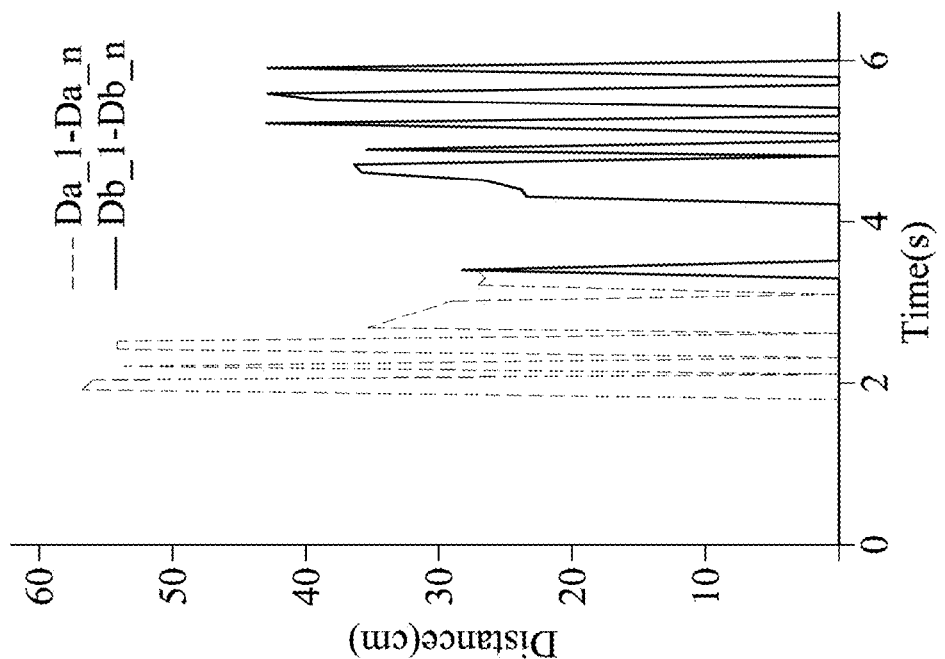
FIG. 4A shows an illustrative line chart depicted according to raw data of distance generated by the location sensing system when the patient passes through the front of the location sensing system.

For example, FIG. 4A shows an illustrative line chart depicted according to raw data of the first distances Da_1-Da_n and the second distances Db_1-Db_n generated by the location sensing system 120A when the patient passes through the front of the location sensing system 120A, such as the patient gets up at the head of the bed (e.g., the plate component 105a) and moves to the end of the bed (e.g., the plate component 105b). Since ultrasonic waves may be absorbed by blanket or clothing of the patient, distance values of multiple time points of this line chart change to zero suddenly, rendering the line chart has multiple missing data and be unfavorable for following analyzation. Therefore, the control circuit 130 is configured to perform a first optimizing calculation and a second optimizing calculation for multiple times to respectively generate multiple first optimized distances ODa_1-ODa_n and multiple second optimized distances ODb_1-ODb_n to compensate the missing data.

In specific, the first optimizing calculation includes: selecting M successive first distances from the first distances Da_1-Da_n; and selecting one of the M successive first distances having a predetermined feature as one of the first optimized distances ODa_1-ODa_n. The second optimizing calculation includes: selecting M successive second distances from the second distances Db_1-Db_n; and selecting one of the M successive second distances having the predetermined feature as one of the second optimized distances ODb_1-ODb_n. In some embodiments, the aforesaid predetermined feature of the first optimizing calculation may be "having the maximum value among the M first distances," "having an average value of the M first distances," or "having the minimum value among the M first distances." In some embodiments, the aforesaid predetermined feature of the second optimizing calculation may be "having the maximum value among the M second distances," "having an average value of the M second distances," or "having the minimum value among the M second distances."

FIG. 4B shows an illustrative line chart depicted according to the first optimized distances ODa_1-ODa_n and the second optimized distances ODb_1-ODb_n. As can be appreciated from FIG. 4B, the aforesaid first optimizing calculation and the second optimizing calculation successfully fill the missing values and efficiently reduce the amount of erroneous values caused by the ultrasonic waves being absorbed, favorable following analyzations regarding the current behavior of the patient. Then, the control circuit 130 subtracts the first optimized distances ODa_1-ODa_n with the second optimized distances ODb_1-ODb_n to obtain multiple coordinate points on the time axis. The control circuit 130 calculates multiple features shown in FIGS. 5A-5D according to these coordinate points, and determines the current behavior of the patient according to those features.

Figure 5B:
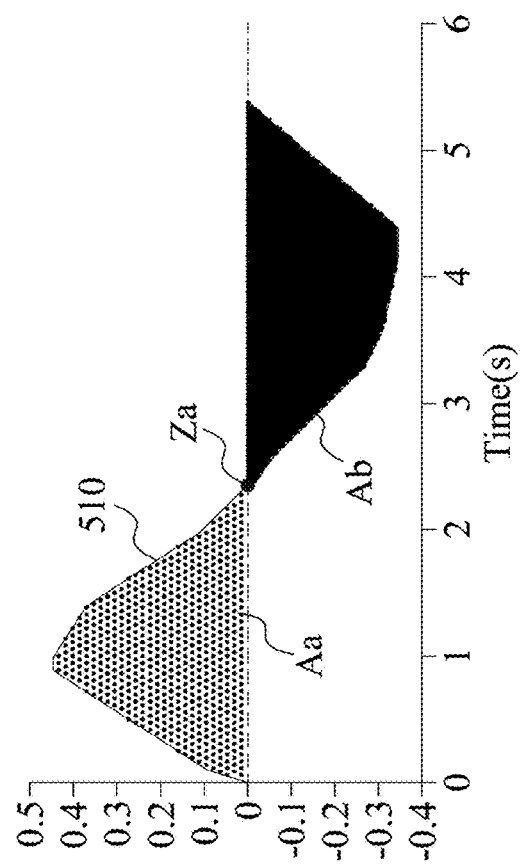
FIG. 5B is for illustrating areas above and below a time axis which are enclosed by the curve of FIG. 5A.
Figure 5A:
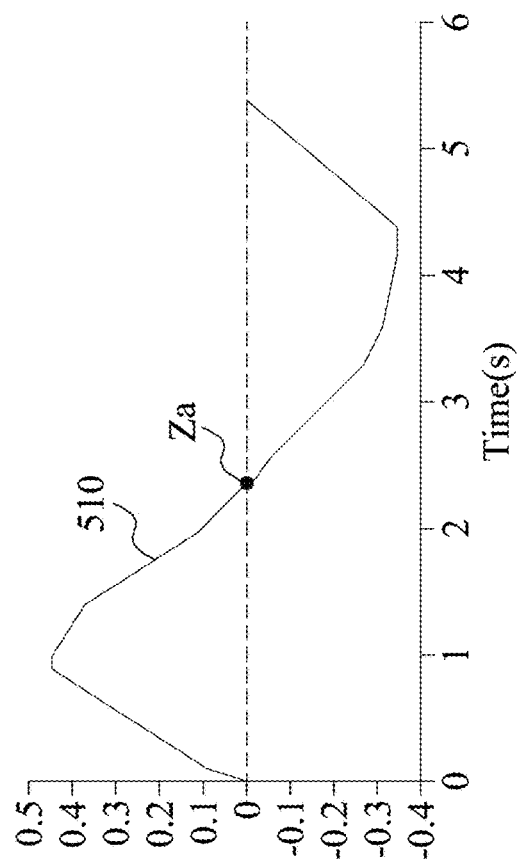
FIG. 5A is for illustrating a zero-crossing point of a curve formed by subtracting the first optimized distances with the second optimized distances.

In this embodiment, since the patient moves from the head to the end of the bed, the first optimized distances ODa_1-ODa_n are positive in a first half of the time axis and approximate to zero in a second half of the time axis. Therefore, a curve 510 is shown in FIGS. 5A-5C, which is formed by those multiple coordinate points obtained from subtracting the first optimized distances ODa_1-ODa_n with the second optimized distances ODb_1-ODb_n. The curve 510 has positive values in the first half of the time axis and has negative values in the second half of the time axis.

Reference is first made to FIG. 5A. The control circuit 130 calculates a number of zero-crossing points of the curve 510, that is, the times that the curve 510 intersects with the time axis. For example, the curve 510 has a zero-crossing point Za. The number of zero-crossing points is for determining the times that the patient passes through the front of the location sensing system 120A.

Referring to FIG. 5B, an area is formed by a portion of the curve 510 above the time axis and another area is formed by another portion of the curve 510 below the time axis, and the control circuit 130 calculates a ratio between these two areas. For example, the control circuit 130 calculates a ratio of an area Aa to an area Ab. This area ratio is for preventing erroneously classifying slight movements of the patient into the bed-exit behaviors.

Reference is made to FIG. 5C. The control circuit 130 selects two coordinate points respectively from two sides of each zero-crossing point, such as a coordinate point P1 and a coordinate point P2 at a left side and a right side of the zero-crossing point Za, respectively. Multiple connecting lines are formed by the two coordinate points respectively at the two sides of each zero-crossing point, and the control circuit 130 calculates a sum of slope of all of the connecting lines. For example, the control circuit 130 calculates the slope of a connecting line La formed by the coordinate point P1 and the coordinate point P2. The sum of slope is for determining a moving direction and a moving speed of the body of the patient. FIG. 5D is for illustrating a curve 520 formed by movement of the patient when the patient moves back and forth in front of the location sensing system 120A. The curve 520 has a zero-crossing point Zb and a zero-crossing point Zc. For calculating the sum of slope, the control circuit 130 selects the coordinate point P3 and a coordinate point P4 respectively at two sides of the zero-crossing point Zb, and selects the coordinate point P4 and a coordinate point P5 respectively at two sides of the zero-crossing point Zc. Then, the control circuit 130 calculates the sum of slope of a connecting line Lb and a connecting line Lc, in which the connecting line Lb is formed by the coordinate point P3 and the coordinate point P4 and the connecting line Lc is formed by the coordinate point P4 and the coordinate point P5. In this situation, since the sum of slope approximates to zero, the control circuit 130 may classify the data of FIG. 5D as false alarm or noise.

Figure 5E:
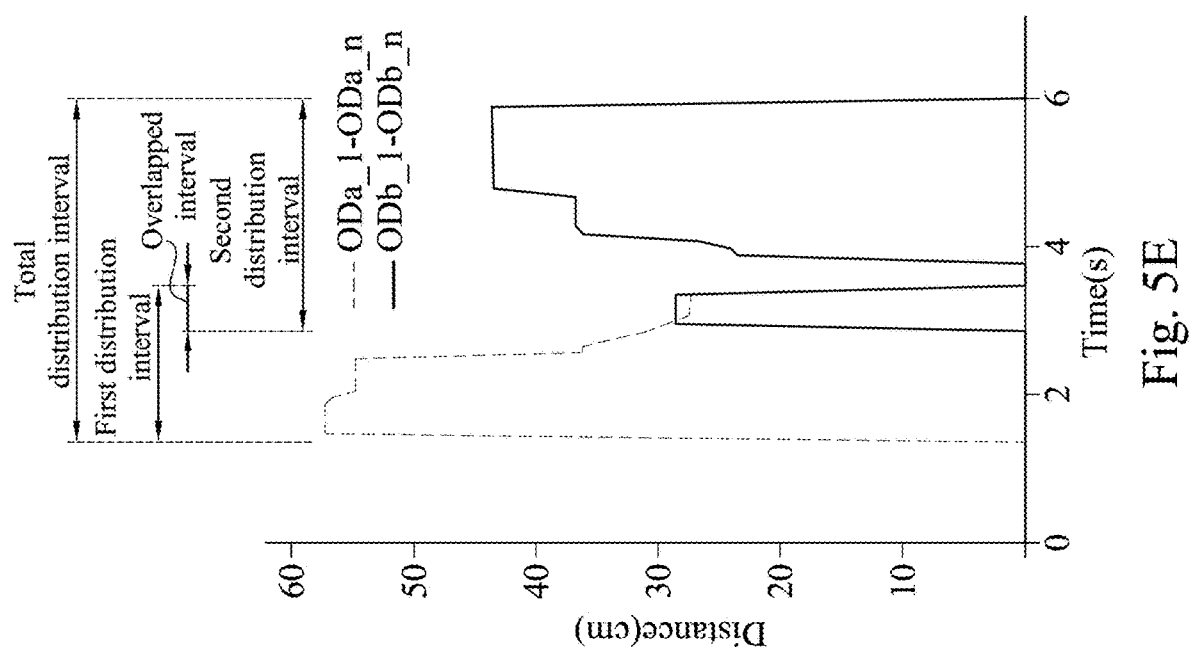
FIG. 5E is for illustrating distribution relationship between the first optimized distances and the second optimized distances on the time axis.

Referring to FIG. 5E, the control circuit 130 is further configured to calculate a total distribution interval of the first optimized distances ODa_1-ODa_n and the second optimized distances ODb_1-ODb_n on the time axis, a first distribution interval of the first optimized distances ODa_1-ODa_n on the time axis, a second distribution interval of the second optimized distances ODb_1-ODb_n on the time axis, and an overlapped interval of the first optimized distances ODa_1-ODa_n and the second optimized distances ODb_1-ODb_n on the time axis. Then, the control circuit 130 calculates a first width ratio of the total distribution interval to the first distribution interval, a second width ratio of the total distribution interval to the second distribution interval, and a third width ratio of the total distribution interval to the overlapped interval.

Accordingly, the control circuit 130 is configured to determine the multiple features of the current behavior of the patient, in which the multiple features include: the number of the zero-crossing points; the ratio between two areas, formed by the curve, respectively above and below the time axis; the sum of slope; the first width ratio; the second width ratio; and the third width ratio. The control circuit 130 may input at least one of these features into a classifier comprising the care data 132, so as to compare these features with multiple sample points of the care data 132 to generate a comparison result. Then, the control circuit 130 determines, according to the comparison result, whether the current behavior of the patient belongs to the multiple bed-exit behaviors or not. In some embodiments, the aforesaid classifier is a k-nearest neighbor classifier, but this disclosure is not limited thereto. Other classifiers suitable for comparing the aforesaid features with the care data 132 are within the contemplated scope of the present disclosure.

As can be appreciated from the foregoing descriptions, the care system 100 of FIG. 1 needs not to upload data to an additional central server when determining the bed-exit behaviors, in which classifying and predicting are performed in devices near a person who is a care recipient. Therefore, the care system 100 would not be affected by system failure and determination delay caused by network congestion, network failure, or insufficient bandwidth, ensuring that the healthcare workers can instantly receive the bed-exit alarm.

Figure 6:
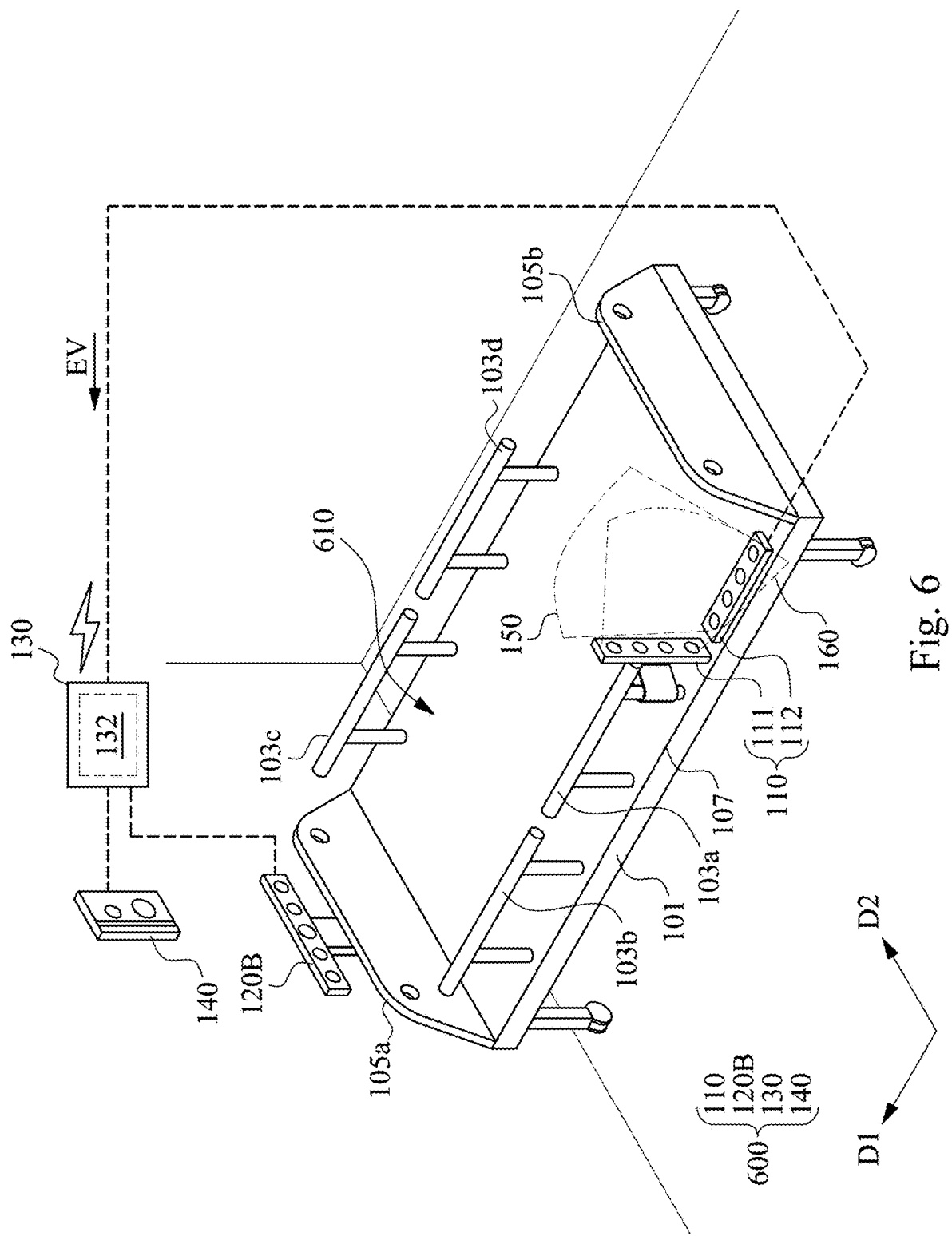
FIG. 6 is a schematic diagram of a care system according to one embodiment of the present disclosure.

FIG. 6 is a schematic diagram of a care system 600 according to one embodiment of the present disclosure. The care system 600 of FIG. 6 is similar to the care system 100 of FIG. 1, and the difference is that the care system 600 replaces the location sensing system 120A with the location sensing system 120B. The location sensing system 120B is configured to be disposed at the plate component 105a or the plate component 105b, that is, the location sensing system 120B has a sensing area aimed to a space 610 of the frame 101 for accommodating the patient. The location sensing system 120B is configured to capture multiple pictures of the patient in the space 610, and configured to provide the captured pictures to the control circuit 130 as the relative position information. The control circuit 130 calculates according to the relative position information and the care data 132 stored in advanced therein to determine whether the current behavior of the patient corresponds to one of the multiple predetermined bed-exit behaviors.

Figure 7:
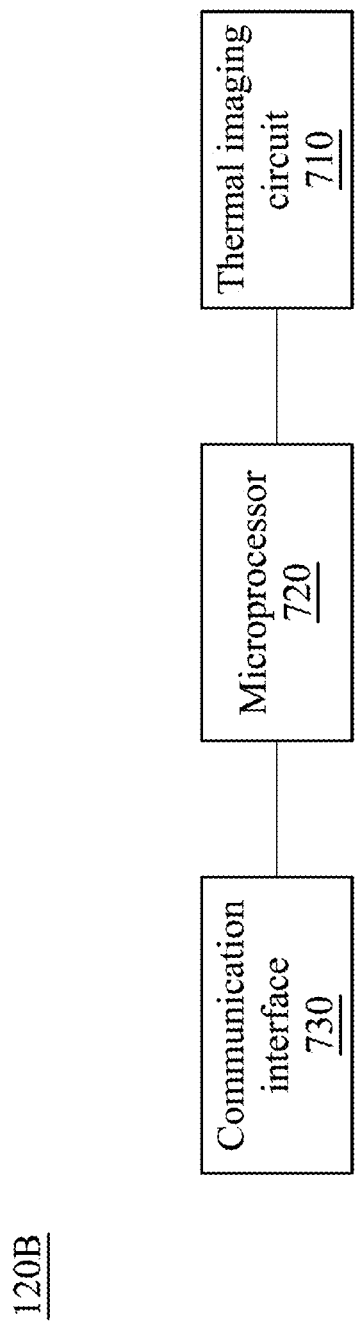
FIG. 7 is a simplified functional block diagram of the location sensing system according to one embodiment of the present disclosure.

FIG. 7 is a simplified functional block diagram of the location sensing system 120B according to one embodiment of the present disclosure. The location sensing system 120B comprises one or more thermal imaging circuits 710 substantially aimed to the space 610, and further comprises a microprocessor 720 and a communication interface 730. The microprocessor 720 is coupled with the thermal imaging circuit 710 and the communication interface 730, and the communication interface 730 is configured to be communicatively coupled with the control circuit 130. In some embodiments, the thermal imaging circuit 710 comprises one or more thermal imaging lenses.

Figure 8A:
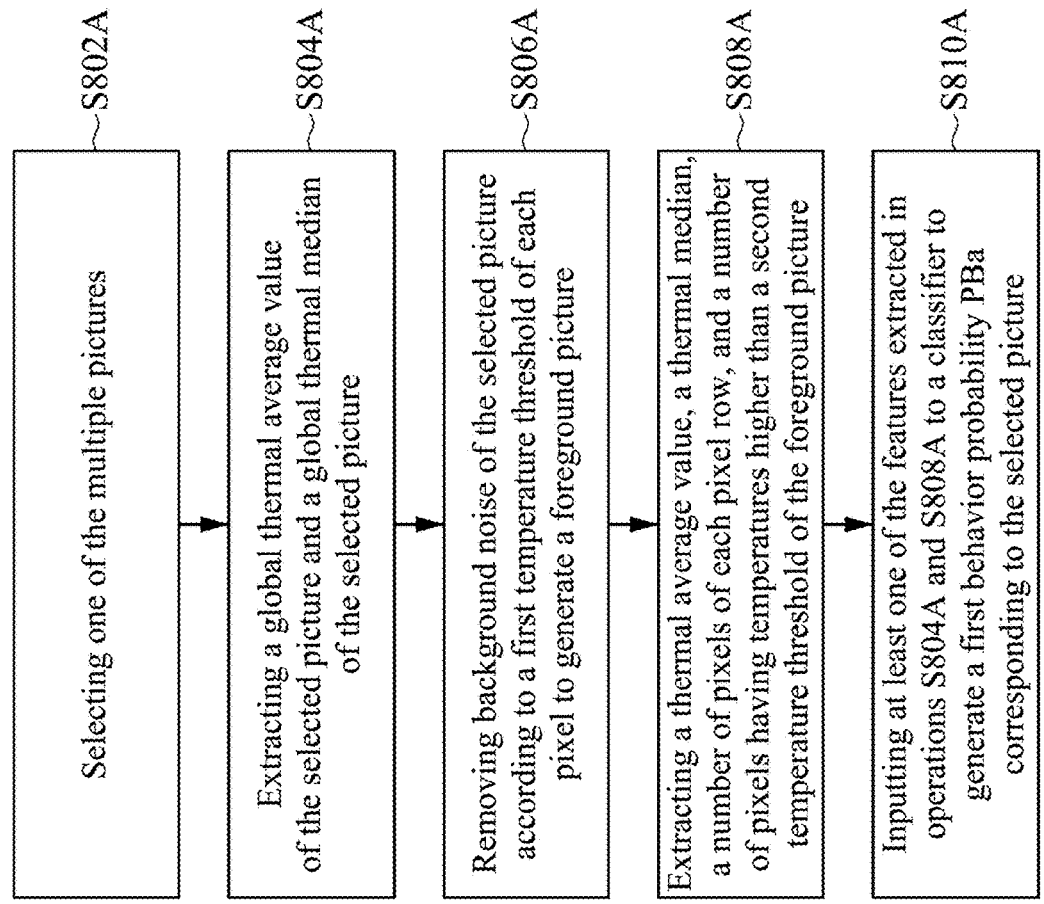
FIG. 8A is a flowchart for generating a behavior probability corresponding to a single picture.
Figure 9B:
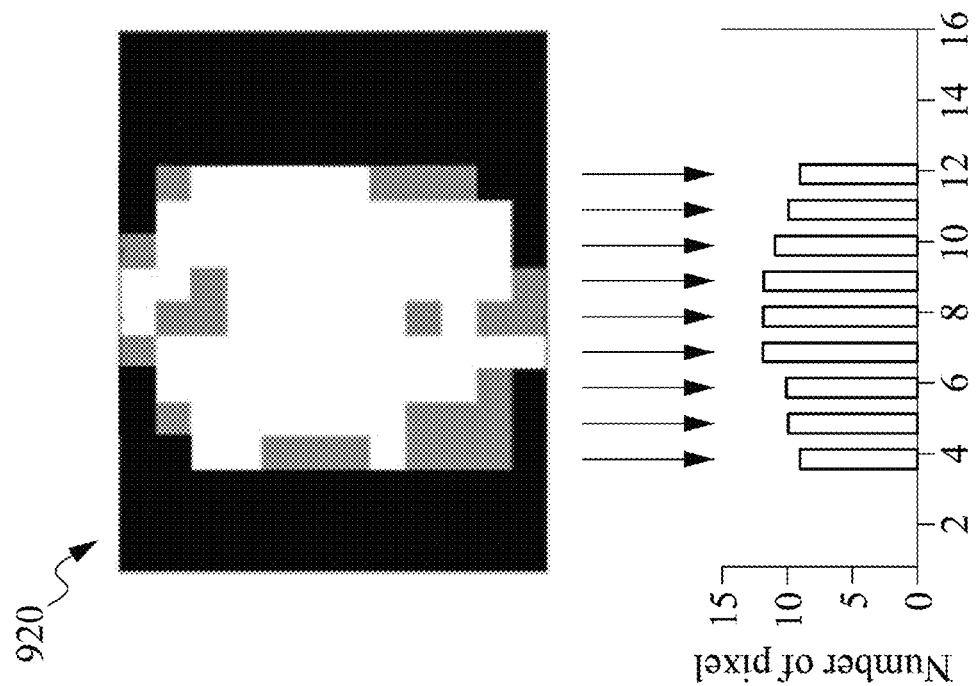
FIG. 9B is for illustrating a foregoing picture generated by filtering out background noise of the picture of FIG. 9A.
Figure 9A:
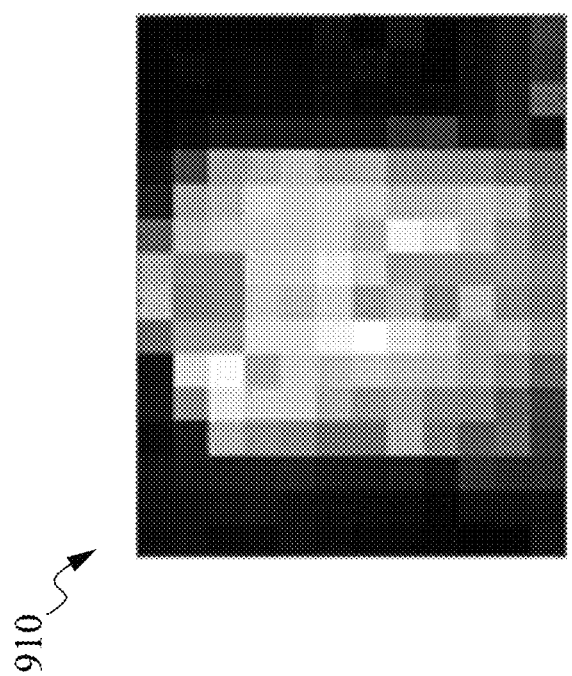
FIG. 9A is for illustrating one of the pictures captured by the location sensing system.

In this embodiment, the control circuit 130 generates different behavior probabilities based on the single picture and the multiple pictures captured by the location sensing system 120B, respectively, and determines whether the patient has the bed-exit behavior or not comprehensively according to those behavior probabilities. For example, the control circuit 130 performs a method 800A of FIG. 8A to generate the behavior probability corresponding to the single picture. In operation S802A, the control circuit 130 selects one of the multiple pictures captured by the location sensing system 120B, which will be explained in reference with the picture 910 of FIG. 9A. In operation S804A, the control circuit 130 extracts the following features: a global thermal average value of pixels of the picture 910; and a global thermal median of the pixels of the picture 910.

In operation S806A, the control circuit 130 removes background noise of the picture 910. For example, the control circuit 130 may use some of the multiple pictures to calculate an average temperature of the pixel at each location in a time period (hereinafter referred to "first temperature threshold"), that is, each pixel of the picture 910 has an independent first temperature threshold. Each pixel of the picture 910 has a temperature lower than the first temperature threshold thereof would be regarded as the background and be filtered out by the control circuit 130 to obtain a foreground picture 920 shown in FIG. 9B. The background which has been filtered out is marked as black pixels. Then, in operation S808A, the control circuit 130 extracts the following features: a thermal average value of the foreground picture 920; a thermal median of the foreground picture 920; a number of pixels of each pixel row of the foreground picture 920; and a number of pixels of the foreground picture 920 having temperatures higher than a second temperature threshold (i.e., the number of the white pixels). In some embodiments, the second temperature threshold is higher than the first temperature threshold of each pixel. Then, in operation S810A, the control circuit 130 inputs at least one of the features extracted in operations S804A and S808A to a classifier to generate the first behavior probability PBa corresponding to the single picture.

In some embodiments, the control circuit 130 provides the features extracted in operations 804A and S808A to four classifiers in operation S810A to respectively generate a first candidate probability, a second candidate probability, a third candidate probability, and a fourth candidate probability. The four classifiers have been trained by machine learning respectively according to four common bed exiting directions, such as the left and the right of the head of the bed and the left and the right of the end of the bed. Therefore, the care data 132 comprises sample points corresponding to the four directions that the patient moves on the frame 101. Then, the control circuit 130 may select the one having the maximum value among the first candidate probability, the second candidate probability, the third candidate probability, and the fourth candidate probability as the first behavior probability PBa.

Figure 8B:
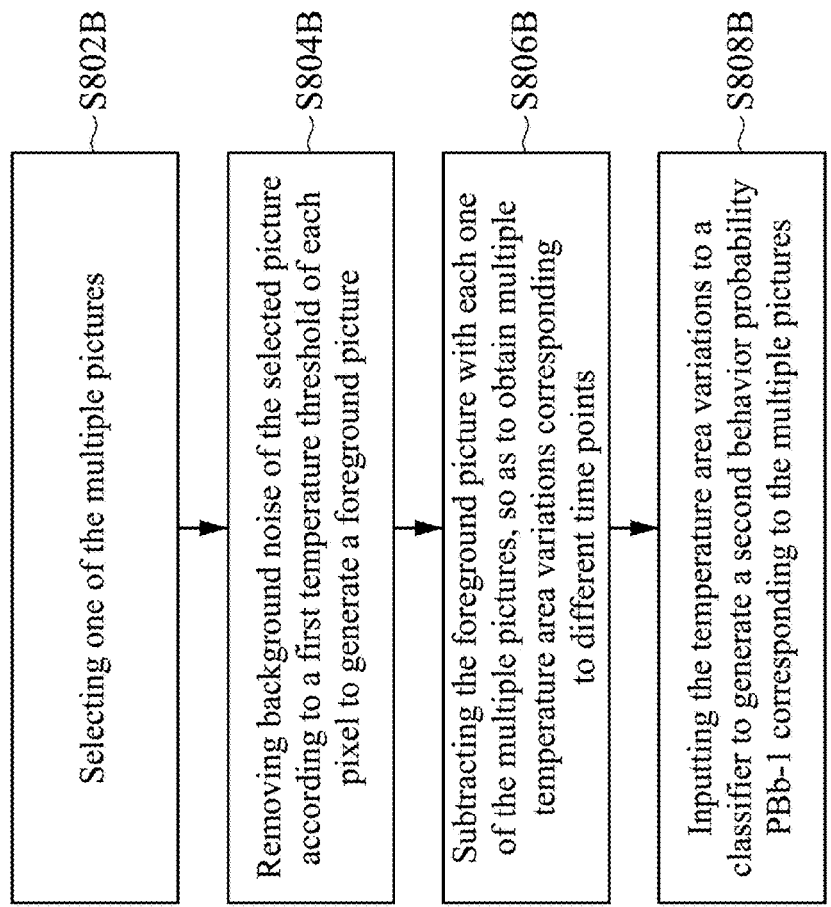
FIG. 8B is a flowchart for generating a behavior probability corresponding to multiple pictures.

The control circuit 130 also performs the method 800B of FIG. 8B to generate the behavior probability corresponding to the multiple pictures. Operations S802B and S804B are similar to operations S802A and S806A, respectively. For the sake of brevity, those descriptions will not be repeated here. In operation S806B, the control circuit 130 subtracts the foreground picture 920 with each one of the multiple pictures captured by the location sensing system 120B, so as to obtain multiple temperature area variations corresponding to different time points. Then, in operation S808B, the control circuit 130 inputs the temperature area variations to a classifier to generate a second behavior probability PBb-1 corresponding to the multiple pictures.

Figure 8C:
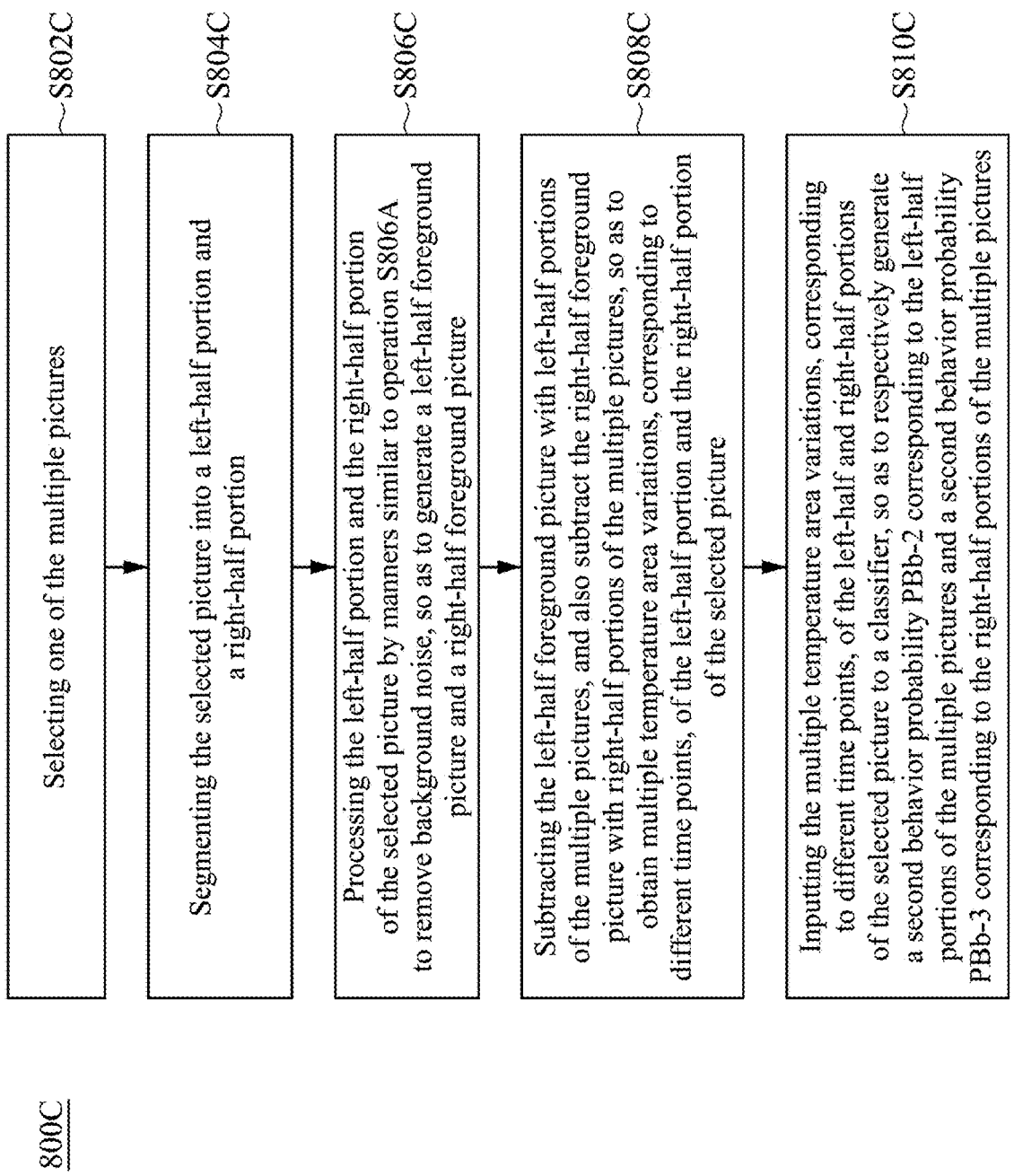
FIG. 8C is a flowchart for generating a behavior probability corresponding to multiple segmented pictures.

In some embodiments, the control circuit 130 further performs a method 800C of FIG. 8C to generate a behavior probability corresponding to multiple segmented pictures. In operation S802C, the control circuit 130 selects one of the multiple pictures captured by the location sensing system 120B, such as the picture 910. Then, in operation S804C, the control circuit 130 segments the selected picture into a left-half portion and a right-half portion. In operation S806C, the control circuit 130 processes the left-half portion and the right-half portion of the picture 910 by manners similar to operation S806A to remove background noise, so as to generate a left-half foreground picture and a right-half foreground picture. For the sake of brevity, those descriptions will not be repeated here.

In operation S808C, the control circuit 130 subtract the left-half foreground picture with left-half portions of the multiple pictures captured by the location sensing system 120B, and also subtract the right-half foreground picture with right-half portions of the multiple pictures captured by the location sensing system 120B, so as to obtain multiple temperature area variations, corresponding to different time points, of the left-half portion and the right-half portion of the selected picture. Then, in operation S810C, the control circuit 130 inputs the multiple temperature area variations, corresponding to different time points, of the left-half portion and the right-half portion of the selected picture to a classifier, so as to respectively generate a second behavior probability PBb-2 corresponding to the left-half portions of the multiple pictures and a second behavior probability PBb-3 corresponding to the right-half portions of the multiple pictures. By performing the method 800C, a moving trend of the body of the patient (e.g., toward left or toward right) can be known, and misjudgment caused by swinging arms of the patient can be reduced.

In operations S808B or S810C of some embodiments, the control circuit 130 may compare the multiple temperature area variations with a look-up table, multiple preset determination rules, or multiple known sample points, so as to generate the second behavior probability PBb-1, PBb-2, or PBb-3.

The control circuit 130 sums up the first behavior probability PBa and the second behavior probabilities PBb-1, PBb-2, and PBb-3 to generate a result of sum. Them, the control circuit 130 determines whether the result of sum is larger than a probability threshold, in which the probability threshold may be stored in a memory circuit (not shown) of the control circuit 130 in advanced. If the sum of result is larger than the probability threshold, the control circuit 130 determines that the current behavior of the patient corresponds to one of the multiple predetermined bed-exit behaviors, and the control circuit 130 transmits a warning signal to the host device 12, the cloud server 16, and the mobile device 18 of the healthcare worker in FIG. 10 to be described later. On the contrary, the control circuit 130 may repeatedly perform the methods 800A, 800B, and 800C.

In some embodiments, the control circuit 130 may perform the methods 800A and 800B, but omit the method 800C. As a result, the control circuit 130 only uses the first behavior probability PBa and the second behavior probability PBb-1 to determine the current behavior of the patient. In other embodiments, the control circuit 130 may perform the methods 800A and 800C, but omitted the method 800B. As a result, the control circuit 130 only uses the first behavior probability PBa and the second behavior probabilities PBb-2 and PBb-3 to determine the current behavior of the patient.

Accordingly, the control circuit 130 may subtract at least a portion of the picture 910 with at least a portion of each of the multiple pictures captured by the location sensing system 120B, so as to determine the current behavior of the patient.

In yet other embodiments, the selected picture may be segmented into multiple portions in operation S804C of the method 800C, so as to generate multiple second behavior probabilities corresponding to these portions in the following operations, in which directions of the segmentations need not be specifically limited.

Notably, the descriptions of the method 800C regarding that the picture 910 is segmented into two portions are merely an exemplary embodiment, in which a number of segmented portions and directions of segmentation may be adjusted based on practical analyzation requirements. In practice, the classifier used in the method 800A, 800B, or 800C may be a random forest classifier or a support vector machine (SVM).

As can be appreciated from the foregoing descriptions, since the care system 600 of FIG. 6 uses thermal imaging technology with low resolution to sense behaviors of the patient, the accuracy of determining bed-exit event can be improved without infringing privacy of the patient. The care system 600 can detect the bed-exit behavior of the patient in an early stage to buy more time for the frontline healthcare workers.

Figure 10:
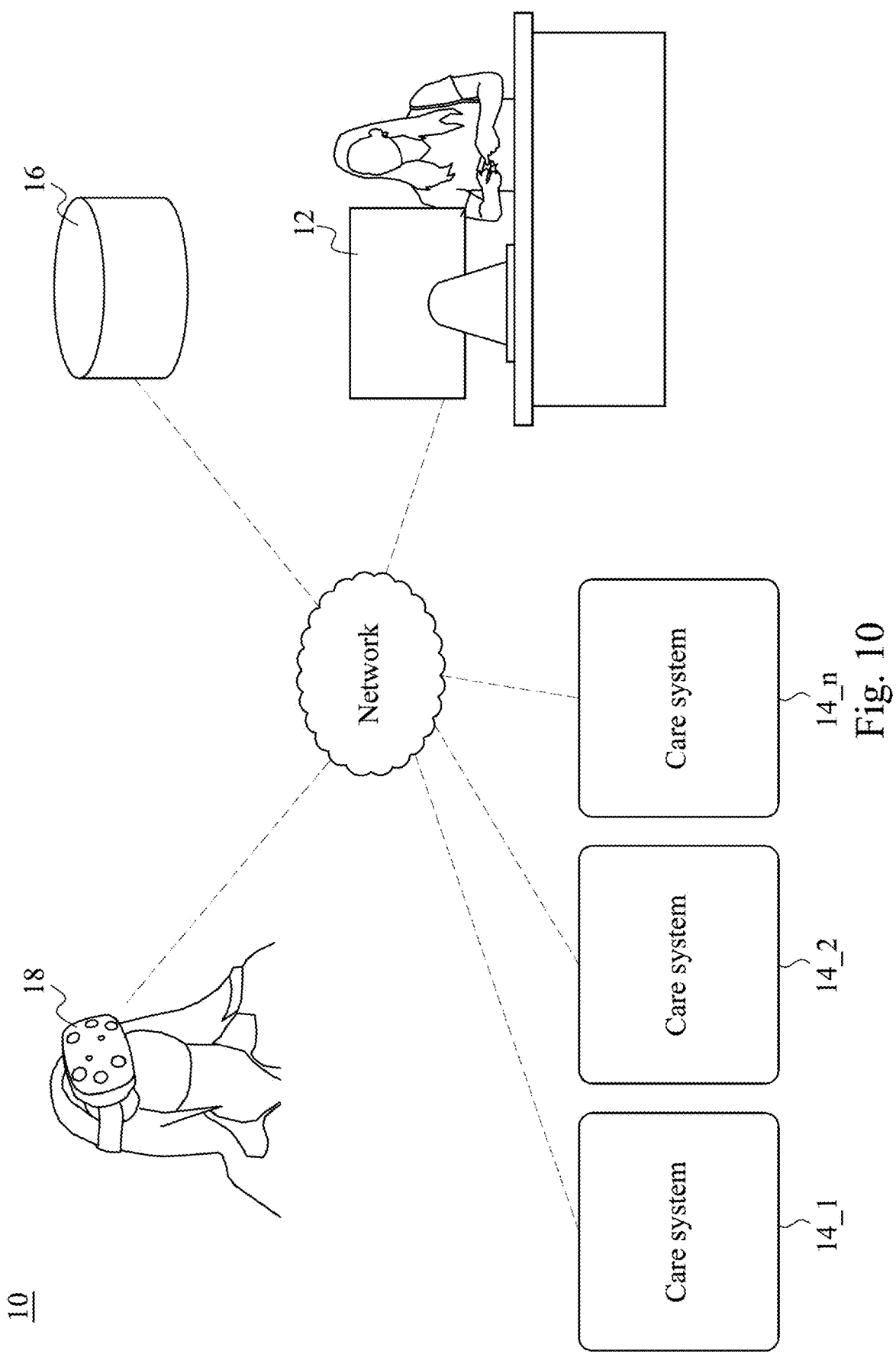
FIG. 10 is a simplified functional block diagram of a patient management system according to one embodiment of the present disclosure.
Figure 11:
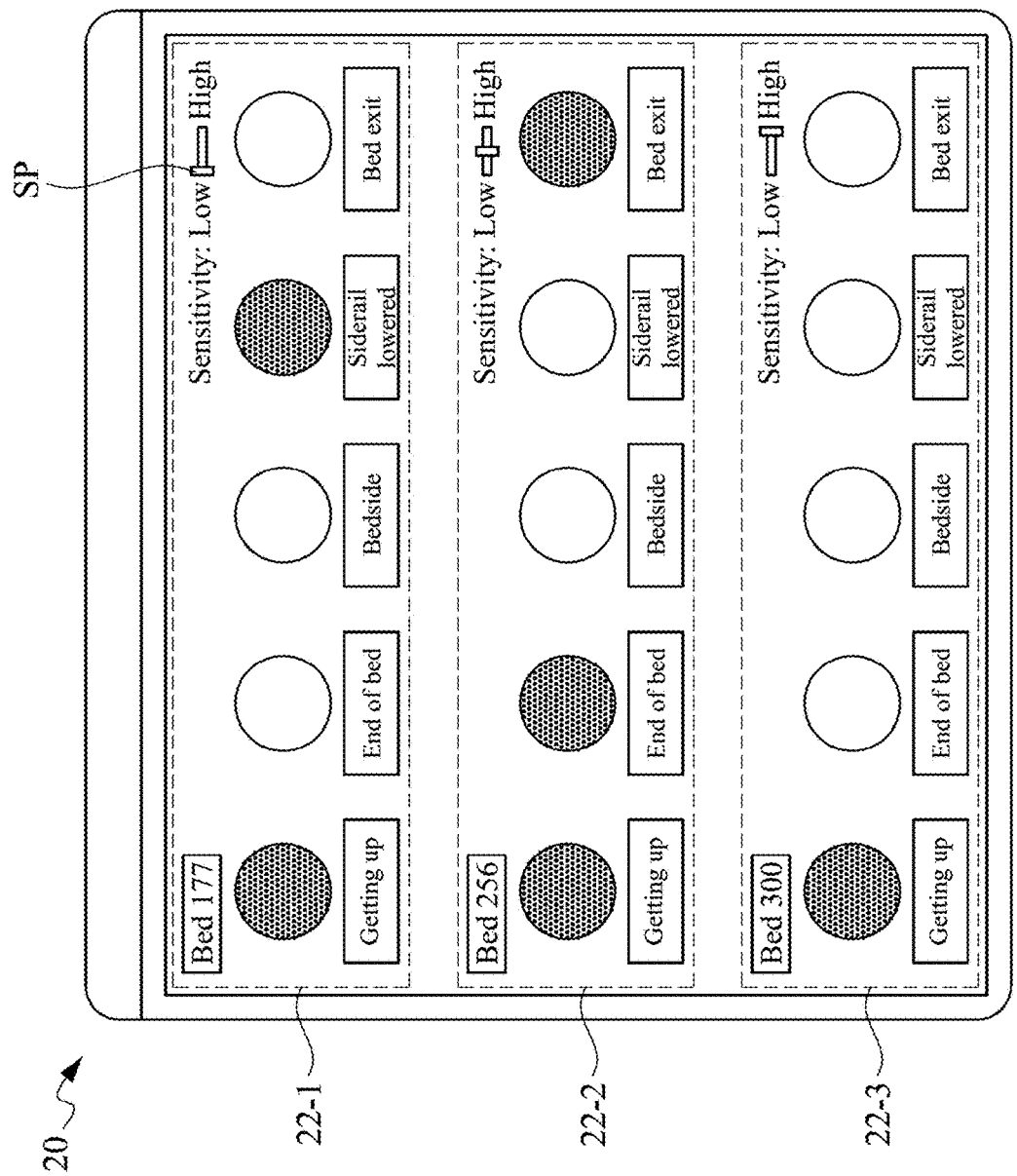
FIG. 11 is a schematic diagram of a host-terminal user interface.

FIG. 10 is a simplified functional block diagram of a patient management system 10 according to one embodiment of the present disclosure. The patient management system 10 comprises the host device 12 and multiple care systems (e.g., care systems 14_1-14_3), in which the care systems 14_1-14_3 are communicatively coupled with the host device 12 through the network. FIG. 11 is a schematic diagram of a host-terminal user interface 20 displayed by the host device 12. The host-terminal user interface 20 comprises multiple display areas 22_1-22_3 corresponding to the care systems 14_1-14_3, respectively. For explanation convenience, "care system 14" is used to refer to any unspecific one among the care systems 14_1-14_3 in the following paragraphs, and "display area 22" is used to refer to any unspecific one among the display areas 22_1-22_3. The number of the care systems of FIG. 10 is merely an exemplary embodiment. In practice, the number of the care systems can be adjusted according to practical requirements of the medical institution.

In some embodiments, the host device 12 may be a personal computer, a notebook computer, or a server at a nursing station of the medical institution. Each of the care systems 14_1-14_3 may be implemented by the care system 100 of FIG. 1 or the care system 600 of FIG. 6. That is, when the care systems 14_1-14_3 determine that the current behavior of the patient matches up to one of the multiple predetermined bed-exit behaviors, the care systems 14_1-14_3 transmit the warning signals to the host device 12.

As shown in FIG. 11, the display area 22 is configured to display the current behavior of the patient determined by the care system 14. For example, a patient of bed 117 is lowering the siderail; a patient of bed 256 has moved to the end of the bed, and thereby matching up to the bed-exit behavior; and a patient of bed 300 is getting up. The display area 22 further comprising a sensitivity adjustment image SP. Then sensitivity adjustment image SP is a user-interactive object, in which the host device 12 is configured to sense an input of a cursor corresponding to a location of the sensitivity adjustment image SP. When the input of the cursor moves successively, the sensitivity adjustment image SP is moved along with the input of the cursor. In other words, a user of the host device 12 can use the cursor to drag the sensitivity adjustment image SP.

The sensitivity adjustment image SP may be moved between three predetermined positions, which represent low sensitivity, medium sensitivity, and high sensitivity, respectively. The three predetermined positions stand for different occasions the control circuit 130 transmits the warning signal to the host device 12. For example, when the sensitivity adjustment image SP is at the position of high sensitivity, the care system 14 transmits the warning signal when determining the current behavior of the patient is "getting up." As another example, when the sensitivity adjustment image SP is at the position of medium sensitivity, the care system 14 transmits the warning signal when determining the current behavior of the patient is "moving to the end of the bed." As yet another example, when the sensitivity adjustment image SP is at the position of low sensitivity, the care system 14 transmits the warning signal when determining the current behavior of the patient is "sitting on the bedside."

Accordingly, the control circuit 130 transmits the warning signal when the current behavior of the patient matching up to one of the bed-exit behaviors. By dragging the sensitivity adjustment image SP, the bed-exit behavior recorded by the control circuit 130 would be changed to another bed-exit behavior, so as to adaptively set different occasions of transmitting warning signal for patients of different care systems 14. When the host device 12 receives the warning signal, an icon of "Bed exit" of the display area 22 may display a predetermined color, flickering light, or a combination thereof.

Reference is made to FIG. 10 again. In some embodiments, the patient management system 10 further comprises a cloud server 16 and a mobile device 18. The cloud server 16 and the mobile device 18 may be communicatively coupled with the host device 12 and the care systems 14_1-14_3 through network. The warning signals of the care systems 14_1-14_3 are not only transmitted to the host device 12, but also are inputted to the cloud server 16. The mobile device 18 is configured to search for multiple times (e.g., periodically) whether a new warning signal is inputted to the cloud server 16. If so, the mobile device 18 retrieve information regarding the new warning signal, such as an actual geographic location information and IP address of the care system 14 transmitting the new warning signal and medical record information of the patient.

The mobile device 18 may send a connecting requirement, based on the obtained IP address, to the audio and video capturing device 140 of the care system 14. When the audio and video capturing device 140 receive the connecting requirement from the mobile device 18, the audio and video capturing device 140 enables a camera, a speaker, and a microphone to capture audio and one or more pictures of the patient. The audio and video capturing device 140 further transmits the captured pictures and audio to the mobile device 18 through video streaming and audio streaming, so that the healthcare worker can find out the current states of the patient and conduct a remote call through the mobile device 18.

Figure 12:
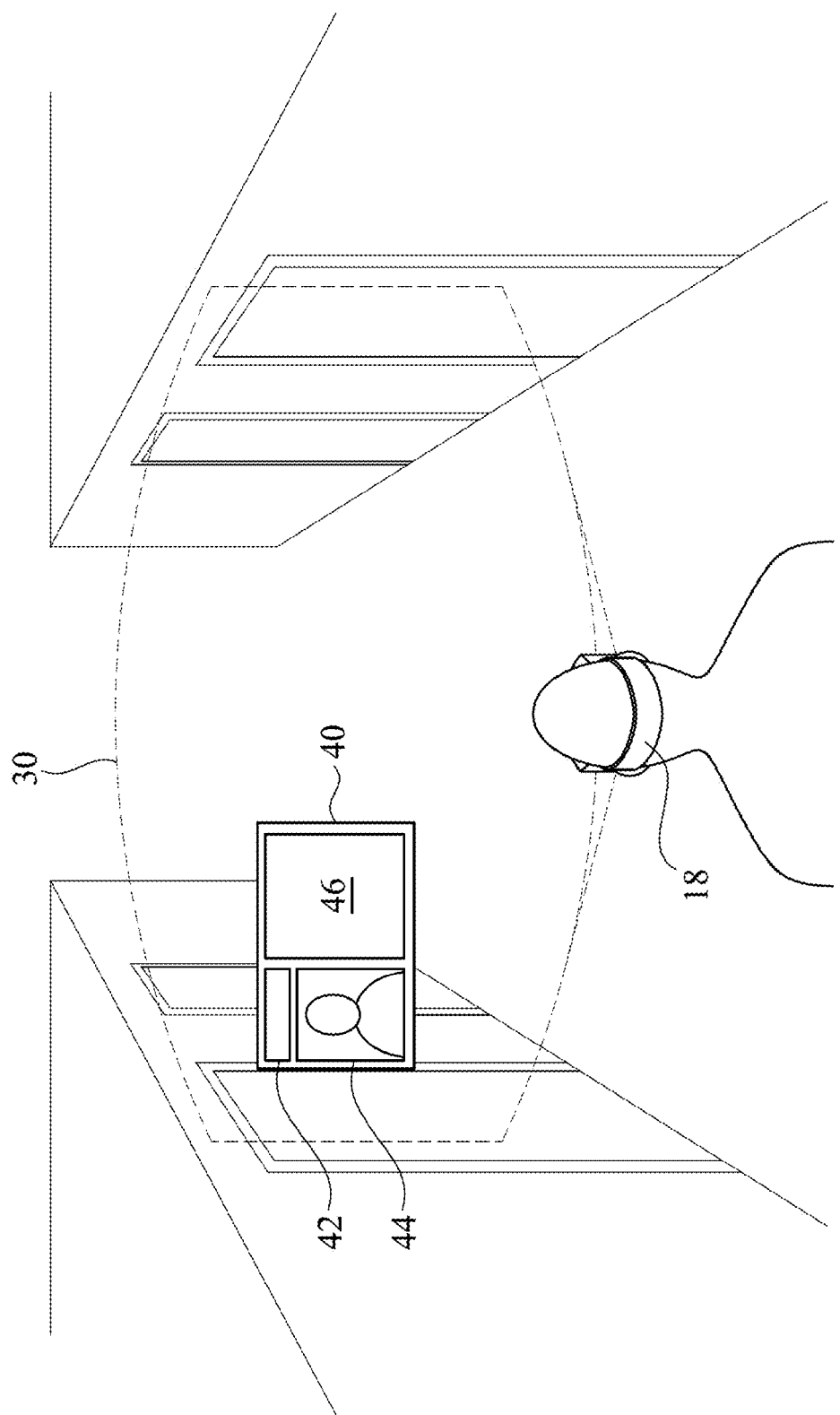
FIG. 12 is for illustrating a visual field of a user of a mobile device.

In practice, the mobile device 18 may be implemented by a smartphone, a tablet, or a head-mounted device (HMD). In some embodiments that the mobile device 18 is implemented by an HMD, as shown in FIG. 12, the mobile device 18 may use the augmented reality (AR) technology or the mixed reality (MR) technology to provide information regarding the warning signal to the user through a mobile-terminal user interface 40 within the visual field 30 of the user. The mobile-terminal user interface 40 comprises geographic location information 42 of the care system 14, medical record information 44 of the patient of the care system 14, and a real-time video area 46. The real-time video area 46 is configured to display the one or more pictures that the mobile device 18 received from the audio and video capturing device 140 through the video stream.

As can be appreciated from the foregoing descriptions, the patient management system 10 provides diverse channels and platforms for obtaining information. Therefore, whether on duty at the nursing station, performing daily inspections, or preparing medicines, healthcare worker can instantly grasp the exit-bed alarm of the patient, so as to comprehensively improve the hospitalization safety of the patients.

Certain terms are used throughout the description and the claims to refer to particular components. One skilled in the art appreciates that a component may be referred to as different names. This disclosure does not intend to distinguish between components that differ in name but not in function. In the description and in the claims, the term "comprise" is used in an open-ended fashion, and thus should be interpreted to mean "include, but not limited to." The term "couple" is intended to compass any indirect or direct connection. Accordingly, if this disclosure mentioned that a first device is coupled with a second device, it means that the first device may be directly or indirectly connected to the second device through electrical connections, wireless communications, optical communications, or other signal connections with/without other intermediate devices or connection means.

The term "and/or" may comprise any and all combinations of one or more of the associated listed items. In addition, the singular forms "a," "an," and "the" herein are intended to comprise the plural forms as well, unless the context clearly indicates otherwise.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A care system, configured to predict bed exit and suitable for a frame configured to support a patient, comprising:
at least one boundary-crossing detection system, configured to be coupled with the frame;
a location sensing system, configured to be coupled with the frame, and configured to obtain relative position information between the patient and the frame; and
a control circuit, configured to data communicate with the at least one boundary-crossing detection system and the location sensing system, and configured to access care data configured to define a plurality of bed-exit behaviors performed by the patient on the frame,
wherein when at least one of following situations occurs, the control circuit transmits a warning signal: (1) the control circuit determines that, according to the relative position information and the care data, a current behavior of the patient corresponds to one of the plurality of bed-exit behaviors; and (2) the at least one boundary-crossing detection system senses that an object is passing through,
wherein a siderail is coupled with a side of the frame which is in parallel with a first direction, a plate component is coupled with other side of the frame which is in parallel with a second direction, and the at least one boundary-crossing detection system comprises:
a first distance sensor, configured to be coupled with the siderail, and having a first sensing area; and
a second distance sensor, configured to be coupled with the side of the frame which is in parallel with the first direction or to be coupled with the plate component, and having a second sensing area,
wherein when the siderail is at an up position, the first sensing area at least partially overlaps with the second sensing area,
wherein the first distance sensor comprises a tri-axial accelerometer, when the tri-axial accelerometer senses that the siderail is changed from the up position to a down position, the control circuit transmits the warning signal.

2. The care system of claim 1, wherein each of the first distance sensor and the second distance sensor comprises one or more infrared transceiver circuits.

3. The care system of claim 1, wherein the location sensing system comprises:
a first location sensor, configured to obtain a plurality of first distances, substantially corresponding to an up-half portion of the frame, between the first location sensor and the patient; and
a second location sensor, configured to obtain a plurality of second distances, substantially corresponding to a bottom-half portion of the frame, between the second location sensor and the patient,
wherein the relative position information comprises the plurality of first distances and the plurality of second distances.

4. The care system of claim 3, wherein the control circuit is adapted to perform a first optimizing calculation and a second optimizing calculation for a plurality of times to respectively obtain a plurality of first optimized distances and a plurality of second optimized distances on a coordinate axis with a unit of time,
the first optimizing calculation comprises: selecting M successive first distances from the plurality of first distances, and selecting one of the M successive first distances having a predetermined feature as one of the plurality of first optimized distances, wherein M is a positive integer,
the second optimizing calculation comprises: selecting M successive second distances from the plurality of second distances, and selecting one of the M successive second distances having another predetermined feature as one of the plurality of second optimized distances,
wherein the control circuit determines the current behavior of the patient according to the plurality of first optimized distances, the plurality of second optimized distances, and the care data.

5. The care system of claim 4, wherein the control circuit is adapted to subtract the plurality of first optimized distances with the plurality of second optimized distances to obtain a plurality of coordinate points on a time axis, and to calculate a plurality of features according to the plurality of coordinate points so as to determine the current behavior of the patient according to at least one of the plurality of features and the care data.

6. The care system of claim 5, wherein the plurality of features comprise:
a number of zero-crossing points of a curve formed by the plurality of coordinate points;
a ratio of an area of a graph above the time axis to an area of the graph below the time axis, wherein the graph is enclosed by the curve and the time axis; and
a sum of slope of multiple connecting lines, wherein the connecting lines are formed by two coordinate points at two sides of each of the zero-crossing points among the plurality of coordinate points.

7. The care system of claim 5, wherein the plurality of features comprise:
a total distribution interval of the plurality of first optimized distances and the plurality of second optimized distances on the time axis;
a first width ratio of the total distribution interval to a first distribution interval of the plurality of first optimized distances on the time axis;
a second width ratio of the total distribution interval to a second distribution interval of the plurality of second optimized distances on the time axis; and
a third width ratio of the total distribution interval to an overlapped interval of the plurality of first optimized distances and the plurality of second optimized distances on the time axis.

8. The care system of claim 7, wherein the control circuit is adapted to provide at least one of the plurality of features to a classifier comprising the care data,
the classifier compares the at least one of the plurality of features with a plurality of sample points of the care data to generate a comparison result, and the control circuit determines the current behavior of the patient according to the comparison result.

9. The care system of claim 3, wherein the first location sensor and the second location sensor are ultrasonic sensors.

10. The care system of claim 1, wherein the location sensing system comprises:
a thermal imaging circuit, configured to capture a plurality of pictures corresponding to a space of the frame for accommodating the patient, wherein the relative position information comprises the plurality of pictures.

11. The care system of claim 10, wherein the control circuit is adapted to capture at least one of a plurality of features from a plurality of pixels of one of the plurality of pictures to determine the current behavior of the patient according to the at least one of the plurality of features and the care data, and the plurality of features comprises:
a global thermal average value of the plurality of pixels;
a global thermal median of the plurality of pixels;
a thermal average value of a foreground picture, wherein an average temperature of each of the plurality of pixels in a time period is set as a first temperature threshold of the pixel, and each pixel of the foreground picture has a temperature higher than the first temperature threshold;
a thermal median of the foreground picture;
a total number of pixels of the foreground picture;
a number of pixels of each pixel row of the foreground picture; and
a number of pixels of the foreground picture having temperatures higher than a second temperature threshold, wherein the second temperature threshold is higher than the first temperature threshold of each of the plurality of pixels.

12. The care system of claim 11, wherein the control circuit is adapted to subtract at least a portion of the one of the plurality of pictures with at least a portion of each of the plurality of pictures to obtain a plurality of temperature area variations corresponding to a plurality of time points, and the control circuit is further adapted to:
generate a first behavior probability according to the at least one of the plurality of features and the care data;
generate one or more second behavior probabilities according to the plurality of temperature area variations and the care data; and
if a sum of the first behavior probability and the one or more second behavior probabilities is larger than a probability threshold, determine the current behavior of the patient corresponds to the one of the plurality of bed-exit behaviors.

13. The care system of claim 12, wherein the control circuit is adapted to provide the at least one of the plurality of features to one or more classifiers to obtain the first behavior probability,
the control circuit is further adapted to provide the plurality of temperature area variations to another classifier, or to compare the plurality of temperature area variations with a look-up table, a plurality of preset determination rules, or a plurality of known sample points, so as to obtain the one or more second behavior probabilities.

14. The care system of claim 13, wherein the one or more classifiers comprise four classifiers, the four classifiers respectively comprise sample points of the care data corresponding to four moving directions of the patient moving on the frame,
the control circuit is adapted to select a maximum one from a first candidate probability, a second candidate probability, a third candidate probability, and a fourth candidate probability outputted by the four classifiers, respectively, as the first behavior probability.

15. A patient management system, comprising:
one or more care systems, wherein each care system is suitable for a frame configured to support a patient, and comprises:

at least one boundary-crossing detection system, configured to be coupled with the frame;
a location sensing system, configured to be coupled with the frame, and configured to obtain relative position information between the patient and the frame; and
a control circuit, configured to data communicate with the at least one boundary-crossing detection system and the location sensing system, and configured to access care data configured to define a plurality of bed-exit behaviors performed by the patient on the frame, wherein when at least one of following situations occurs, the control circuit transmits a warning signal: (1) the control circuit determines that, according to the relative position information and the care data, a current behavior of the patient corresponds to one of the plurality of bed-exit behaviors; and (2) the at least one boundary-crossing detection system senses that an object is passing through; and
a host device, configured to data communicate with the control circuit to receive and display correspondingly the warning signal, and configured to provide a host-terminal user interface, wherein the host-terminal user interface comprises one or more sensitivity adjustment images corresponding to the one or more care systems, respectively,
wherein each sensitivity adjustment image is an user-interactive object, when the sensitivity adjustment image is moved from a first predetermined area to a second predetermined area, the control circuit of one of the one or more care systems corresponding to the sensitivity adjustment image changes the one of the plurality of bed-exit behaviors to other one of the plurality of bed-exit behaviors,
wherein a siderail is coupled with a side of the frame in parallel with a first direction, and a plate component is coupled with other side of the frame in parallel with a second direction, and the at least one boundary-crossing detection system comprises:
a first distance sensor, configured to be coupled with the siderail, and has a first sensing area; and
a second distance sensor, configured to be coupled with the side of the frame in parallel with the first direction, or configured to be coupled with the plate component, and has a second sensing area,
wherein when the siderail is at an up position, the first sensing area at least partially overlaps with the second sensing area,
wherein the first distance sensor comprises a tri-axial accelerometer, when the tri-axial accelerometer senses that the siderail is changed from the up position to a down position, the control circuit transmits the warning signal.

16. The patient management system of claim 15, further comprising:
a cloud server, configured to receive the warning signal from the control circuit and to store the warning signal;
a mobile device, configured to access the cloud server to determine whether the cloud server stores the warning signal; and
an audio and video capturing device, configured to data communicate with the mobile device,
wherein when the mobile device determines that the cloud server receives the warning signal, the mobile device is adapted to:
instruct the audio and video capturing device of a care system of the one or more care systems corresponding to the warning signal to capture one or more pictures, and to transmit the one or more pictures to the mobile device by video streaming; and
perform a voice communication with the audio and video capturing device of the care system corresponding to the warning signal.

17. The patient management system of claim 16, wherein the mobile device is configured to display a mobile-terminal user interface comprising:
a geographic location information of the care system corresponding to the warning signal;
medical record information of the patient of the care system corresponding to the warning signal; and
a real-time video area, configured to display the one or more pictures received by the mobile device through the video streaming.

* * * * *